US006984660B2

(12) United States Patent
Heitsch

(10) Patent No.: US 6,984,660 B2
(45) Date of Patent: Jan. 10, 2006

(54) P-THIENYLBENZYLAMIDES AS AGONISTS OF ANGIOTENSIN-(1-7) RECEPTORS, AND METHODS OF THEIR PREPARATION AND USE

(75) Inventor: Holger Heitsch, Mainz-Kastel (DE)

(73) Assignee: Aventis Pharma Deutschland GmbH, Frankfurt am Main (DE)

(*) Notice: Subject to any disclaimer, the term of this patent is extended or adjusted under 35 U.S.C. 154(b) by 0 days.

(21) Appl. No.: 10/310,055

(22) Filed: Dec. 5, 2002

(65) Prior Publication Data
US 2003/0144343 A1 Jul. 31, 2003

Related U.S. Application Data

(62) Division of application No. 10/095,584, filed on Mar. 13, 2002, now Pat. No. 6,538,144.

(30) Foreign Application Priority Data
Mar. 14, 2001 (DE) .......................... 101 12 041

(51) Int. Cl.
A61K 31/381 (2006.01)

(52) U.S. Cl. ...................... 514/444; 514/445
(58) Field of Classification Search ................. 514/444, 514/445
See application file for complete search history.

(56) References Cited

U.S. PATENT DOCUMENTS 6,235,766 B1   5/2001   Heitsch et al.
6,429,222 B2   8/2002   Heitsch et al.

FOREIGN PATENT DOCUMENTS

EP   0 512 675 A1   11/1992
EP   0 513 979 A1   11/1992
GB   2 281 298 A    3/1995
WO   WO 00/68226   11/2000

OTHER PUBLICATIONS

Loot et al., Circulation, 105: 1548–1550, 2002.
"The Endothelium as a Target and Mediator of Cardiovascular Disease," European Journal of Clinical Investigation, 23: 670–685 (1993).
Benter, et al., "Antihypertensive Actions of Angiotensin–(1–7) in Spontaneously Hypertensive Rats," Journal of Physiology, 269(1): H313–H319 (1995).
Benter, et al., "Cardiovascular Actions of Angiotensin(1–7)," Peptides, 14(4): 679–684 (1993).
Brosnihan, "Effect of the Angiotension–(107) Peptide on Nitric Oxide Release," The American Journal of Cardiology, 82(10A): 17S–19S (1998).
Brosnihan, et al., "Angiotensin–(1–7) Dilates Canine Coronary Arteries Through Kinins and Nitric Oxide," Hypertension, 27(3): 523–528 (1996).
Deprez, et al., "Sulfonylureas and Sulfonylcarbamates as New Non–Tetrazole Angiotensin II Receptor Antagonists. Discovery of a Highly Potent Orally Active (Imidazolylbiphenylyl) Sulfonylurea (HR 720)," Journal of Medicinal Chemistry, 38 (13): 2357–2377 (1995).
Ferrario, et al., "Angiotensin–(1–7): A Bioactive Fragment of the Renin–angiotensin System," Regulatory Peptides, 78: 13–18 (1998).
Ferrario, et al., "Angiotensin–(1–7): A New Hormone of the Angiotensin System," Hypertension, 18(5): 126–133 (1991).
Ferrario, et al., "Charaterization of Angiotensin–(1–7) in the Urine of Normal and Essential Hypertensive Subjects," Hypertension, 11(1): 137–146 (1998).
Ferrario, et al., "Counterregulatory Actions of Angiotensin–(1–7)," Hypertension, 30(3): 535–541 (1997).
Freeman, et al, "Angiotensin–(1–7) Inhibits Vascular Smooth Muscle Cell Growth," Hypertension, 28(1): 104–108 (1996).
Handa, et al., "Renal Actions of Angiotensin–(1–7): In Vivo and In Vitro Studies," American Journal of Physiology, 270(1): 141–147 (1996).
Heitsch, et al., "3–N– Methylviphenylsulfonylurea and –Carbamate Substituted Imidazo [4,5–b] Pyridines. Potent Antagonists of the ANG II $AT_1$ Receptors," Bioorganic & Medicinal Chemistry, 5(4): 673–678 (1997).
Heitsch, et al., "Synthesis of the Imidazole–Derived $AT_1$–Selective ANG II Receptor Antagonist HR 720 Utilizing Reductive Amination as Key Step," Journal of Synthetic Organic Chemistry, 11: 1325–1330 (1990).
Iyer, et al, "Vasodepressor Actions of Angiotensin–(17) Unmasked During Combined Treatment with Lisinopril and Losartan," Hypertension, 31(2): 699–705 (1998).
Jaiswal, et al., "Stimulation of Eendothelial Cell Porstaglandin Production by Angiotensin Peptides," Hypertension, 19(2): 49–55 (1992).
Lane, "Sodium Cyanoborohydride—A Highly Selective Reducing Agent for Organic Functional Groups," International Journal of Methods in Synthetic Organic Chemistry, 3: 135–146 (1975).
Matsumura, et al., "Stereoselective Syntheses of Solenopsin A and B," Tetrahedron Letters, 23(18): 1929–1932 (1982).
Miyaura, et al., "The Palladium–Catalyzed Cross–Coupling Reaction of Phenylvoronic Acid With Haloarenes in the Presence of Bases," Synthetic Communications, 11(7): 513–519 (1981).
Moriarty, et al., "A Revised Structure for the Marine Bromindole Derivative Citorellamine," Tetrahedron Letters, 28(7): 749–752 (1987).
Santos, et al., "Charaterization of a New Angiotensin Antagonist Selective for Angiotensin–(1–7): Evidence That the Actions of Angiotensin–(1–7) are Mediated by Specific Angiotensin Receptors," Brain Research Bulletin, 35(4): 293–298 (1994).
Strawn, et al., "Angiotensin–(1–7) Reduces Smooth Muscle Growth After Vascular Injury," Hypertension, 33(1): 207–211 (1999).
Tallant, et al, "Bovine Aortic Endothelial Cells Contain an Angiotensin–(1–7) Receptor," Hypertension, 29(1) 388–393 (1997).

Tran, et al., "Angiotensin-(1–7) and the Rat Aorta: Modulation by the Endothelium," *Journal of Cardiovascular Pharmacology*, 30(5): 676–682 (1997).

Wiemer, et al., "Production of Cyclic GMP via Activation of B1 and B2 Kinin Receptors in Cultured Bovine Aortic Endothelial Cells," *The Journal of Pharmacology and Experimental Therapeutics*, 262(2): 729–733 (1992).

*Primary Examiner*—Joseph K. McKane
*Assistant Examiner*—Rebecca Anderson
(74) *Attorney, Agent, or Firm*—Finnegan, Henderson, Farabow, Garrett & Dunner, L.L.P.

(57) ABSTRACT

The invention relates to p-thienylbenzylamides of formula (I):

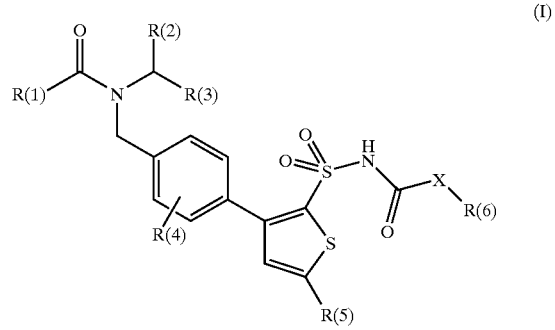

in which R(1), R(2), R(3), R(4), R(5), R(6) and X have the meanings given in the description. The compounds of formula (I) are potent agonists of angiotensin-(1–7) receptors and are useful as pharmaceutically active compounds to treat and/or prevent hypertension; cardiac hypertrophy; cardiac insufficiency; coronary heart diseases, such as angina pectoris; and endothelial dysfunction or endothelial damage as a consequence, for example, of atherosclerotic processes or in association with diabetes mellitus.

1 Claim, No Drawings

P-THIENYLBENZYLAMIDES AS AGONISTS OF ANGIOTENSIN-(1-7) RECEPTORS, AND METHODS OF THEIR PREPARATION AND USE

This is a division of application Ser. No. 10/095,584, filed Mar. 13, 2002, now U.S. Pat. No. 6,538,144, which is incorporated herein by reference.

The invention relates to p-thienylbenzylamides of formula (I):

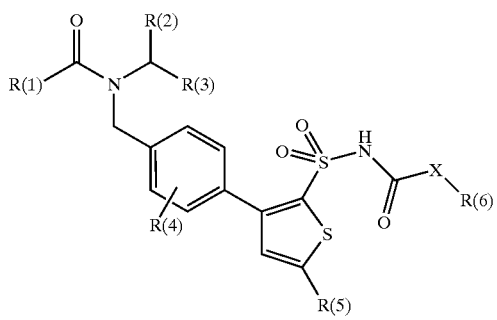

in which R(1), R(2), R(3), R(4), R(5), R(6) and X have the meanings given below. The compounds of formula (I) are potent agonists of angiotensin-(1–7) receptors. As a result of the stimulation of these receptors, which is elicited by the compounds of formula (I), and the production and release of the vasorelaxing and cardioprotective messengers cyclic guanosine monophosphate (cGMP) and nitrogen monoxide (NO) associated with endothelial cells, the compounds of formula (I) are suitable as pharmaceutically active compounds for treating and preventing hypertension; cardiac hypertrophy; cardiac insufficiency; coronary heart diseases, such as angina pectoris; and endothelial dysfunction or endothelial damage, for example, as a consequence of atherosclerotic processes or in association with diabetes mellitus.

PCT application WO-0068226 describes 1-(p-thienylbenzyl)imidazoles as agonists of angiotensin-(1–7) receptors for the treatment and/or prophylaxis of hypertension, cardiac hypertrophy, cardiac insufficiency and endothelial dysfunction or endothelial damage.

In view of the multifarious possibilities for using angiotensin (ANG)-(1–7) receptor agonists as pharmaceuticals, and the demands for such properties, there is a need for further ANG-(1–7) receptor agonists which exhibit favorable activity and selectivity (i.e., a good pharmacodynamic or pharmacokinetic profile).

It has been found, surprisingly, that p-thienylbenzylamides of formula (I) have a pronounced effect on angiotensin-(1–7) receptors and mimic the biological effect of the effector hormone angiotensin-(1–7).

One part of the subject-matter of the invention consequently relates to compounds of formula (I):

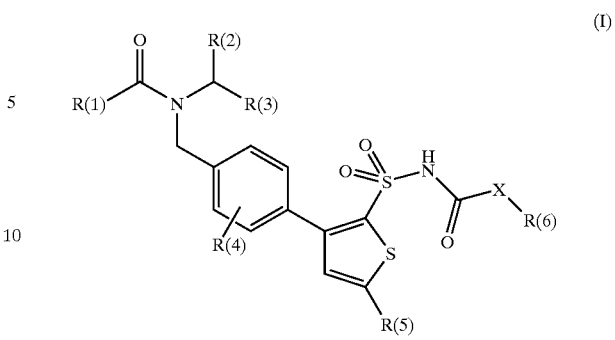

in which the indicated radicals have the following meanings:
R(1) is chosen from among
1. $(C_1-C_5)$-alkyl, unsubstituted or substituted by a radical chosen from among $NH_2$, halogen, O—$(C_1-C_3)$-alkyl, CO—O—$(C_1-C_3)$-alkyl and $CO_2H$;
2. $(C_3-C_8)$-cycloalkyl;
3. $(C_1-C_3)$-alkyl-$(C_3-C_8)$-cycloalkyl;
4. $(C_6-C_{10})$-aryl, unsubstituted or substituted by a radical chosen from halogen and O—$(C_1-C_3)$-alkyl;
5. $(C_1-C_3)$-alkyl-$(C_6-C_{10})$-aryl, where the aryl radical is unsubstituted or substituted by a radical chosen from halogen and O—$(C_1-C_3)$-alkyl;
6. $(C_1-C_5)$-heteroaryl; and
7. $(C_1-C_3)$-alkyl-$(C_1-C_5)$-heteroaryl;
R(2) is chosen from among
1. hydrogen;
2. $(C_1-C_6)$-alkyl, unsubstituted or substituted by a radical chosen from halogen and O—$(C_1-C_3)$-alkyl;
3. $(C_3-C_8)$-cycloalkyl;
4. $(C_1-C_3)$-alkyl-$(C_3-C_8)$-cycloalkyl;
5. $(C_6-C_{10})$-aryl, unsubstituted or substituted by a radical chosen from among halogen, O—$(C_1-C_3)$-alkyl and CO—O—$(C_1-C_3)$-alkyl; and
6. $(C_1-C_3)$-alkyl-$(C_6-C_{10})$-aryl, unsubstituted or substituted by a radical chosen from halogen and O—$(C_1-C_3)$-alkyl;
R(3) is chosen from among
1. hydrogen;
2. COOH; and
3. COO—$(C_1-C_4)$-alkyl;
R(4) is chosen from among
1. hydrogen;
2. halogen; and
3. $(C_1-C_4)$-alkyl;
R(5) is chosen from among
1. hydrogen, and
2. $(C_1-C_6)$-alkyl;
R(6) is chosen from among
1. hydrogen;
2. $(C_1-C_6)$-alkyl;
3. $(C_1-C_3)$-alkyl-$(C_3-C_8)$-cycloalkyl; and
4. $(C_2-C_6)$-alkenyl;
X is chosen from among
1. oxygen, and
2. NH;
in all the stereoisomeric forms thereof, and mixtures thereof in all ratios, and the physiologically tolerated salts thereof.

Unless otherwise indicated, the term alkyl encompasses straight-chain or branched saturated hydrocarbon radicals. This also applies to substituents which are derived therefrom, such as alkoxy or the radicals $SO_2NHCOO$-alkyl and $SO_2NHCONH$-alkyl. Examples of alkyl radicals include methyl, ethyl, n-propyl, isopropyl, isobutyl, n-butyl, n-hexyl, isohexyl and n-heptyl. Examples of alkoxy radicals include methoxy, ethoxy and propoxy, such as n-propoxy and isopropoxy.

Alkenyl denotes singly or multiply unsaturated hydrocarbon radicals in which the double bonds can be present in any arbitrary position. Examples of alkenyl radicals include vinyl, prop-2-enyl (allyl), prop-1-enyl and butenyl.

Examples of cycloalkyl include cyclopropyl, cyclobutyl, cyclopentyl, cyclohexyl, cycloheptyl and cyclooctyl.

Halogen denotes fluorine, chlorine, bromine or iodine, and in one embodiment, the halogen is chlorine or fluorine.

Examples of aryl radicals include phenyl and naphthyl (1- or 2-naphthyl).

In substituted aryl radicals, the substituents can be located in any positions in relation to each other.

Heteroaryl is understood as meaning radicals of monocyclic 5-membered or 6-membered aromatic ring systems. They can be regarded as being radicals which are derived from cyclopentadienyl and phenyl by the replacement of one or two CH groups and/or $CH_2$ groups with S, O, N or NH (or N carrying a substituent, such as N—$CH_3$), in connection with which the aromatic ring system is preserved or an aromatic ring system is formed. In addition to the one, two, three or four ring heteroatoms, they may contain one, two, three, four or five ring carbon atoms (($C_1$–$C_5$)-heteroaryl). Examples of suitable heteroaryls include furanyl, thienyl, pyrrolyl, imidazolyl, triazolyl, tetrazolyl, pyrazolyl, oxazolyl, isoxazolyl, thiazolyl, isothiazolyl, pyridyl, pyrazinyl and pyrimidyl. A heteroaryl radical can be bonded by way of any suitable carbon atom.

In one embodiment, R(1) is
1. ($C_1$–$C_5$)-alkyl, such as methyl; or
2. ($C_1$–$C_5$)-alkyl, substituted by a radical chosen from CO—O—($C_1$–$C_3$)-alkyl and $CO_2H$; such as carboxypropionyl and methoxycarbonylpropionyl; or
3. ($C_1$–$C_3$)-alkyl-($C_3$–$C_8$)-cycloalkyl, such as cyclohexylmethyl; or
4. ($C_6$–$C_{10}$)-aryl, such as phenyl; or
5. ($C_1$–$C_5$)-heteroaryl, such as furanoyl.

R(2) is
1. hydrogen; or
2. ($C_1$–$C_6$)-alkyl, such as isopropyl; or
3. ($C_1$–$C_6$)-alkyl, substituted by O—($C_1$–$C_3$)-alkyl, such as methoxymethylene; or
4. ($C_3$–$C_8$)-cycloalkyl, such as cyclopropyl and cyclohexyl; or
5. ($C_6$–$C_{10}$)-aryl, such as phenyl.

R(3) is
1. COOH; or
2. COO—($C_1$–$C_4$)-alkyl, such as methoxycarbonyl and ethoxycarbonyl.

R(4) is hydrogen.
R(5) is ($C_1$–$C_6$)-alkyl, such as isobutyl.
R(6) is ($C_1$–$C_6$)-alkyl, such as methyl, ethyl or butyl.

The present invention encompasses all the stereoisomeric forms of the compounds of formula (I). In the compounds of formula (I) which contain centers of asymmetry, all these centers can, independently of each other, have the S or R configuration. The invention includes all the possible enantiomers and diastereomers, as well as mixtures of two or more diastereomeric forms, for example mixtures composed of enantiomers and/or diastereomers, in all ratios. When a cis/trans isomerism is present, both the cis and the trans form, and mixtures of these forms in all ratios, are part of the subject-matter of the invention. The invention also encompasses all the tautomeric forms of the compounds of formula (I).

Physiologically tolerated salts of compounds of formula (I) are understood as being both their inorganic salts and their organic salts, as described in Remington's Pharmaceutical Sciences (A. R. Gennard, Editor, Mack Publishing Co, Easton Pa., 17th edition, pages 14–18, 1985). Because of their physiological and chemical stability and solubility, useful salts include, inter alia, sodium, potassium, calcium, magnesium and ammonium salts for acidic groups. Reactions of compounds of formula (I) with bases for the purpose of preparing the salts are, in general, carried out in accordance with customary-procedures in a solvent or diluent.

The present invention furthermore encompasses solvates of compounds of formula (I), for example, hydrates or adducts with alcohols; and also derivatives of the compounds of formula (I), such as esters; and prodrugs and active metabolites.

In another embodiment, the compounds of formula (I) include those in which
R(1) is chosen from among
1. ($C_1$–$C_5$)-alkyl, unsubstituted or substituted by a radical chosen from among $NH_2$, halogen, O—($C_1$–$C_3$)-alkyl, CO—O—($C_1$–$C_3$)-alkyl and $CO_2H$;
2. ($C_3$–$C_6$)-cycloalkyl;
3. ($C_1$–$C_3$)-alkyl-($C_3$–$C_6$)-cycloalkyl;
4. ($C_6$–$C_{10}$)-aryl, unsubstituted or substituted by a radical chosen from halogen and O—($C_1$–$C_3$)-alkyl;
5. ($C_1$–$C_3$)-alkyl-($C_6$–$C_{10}$)-aryl, where the aryl radical is unsubstituted or substituted by a radical chosen from halogen and O—($C_1$–$C_3$)-alkyl;
6. ($C_3$–$C_5$)-heteroaryl; and
7. ($C_1$–$C_3$)-alkyl-($C_3$–$C_5$)-heteroaryl;

R(2) is chosen from among
1. hydrogen;
2. ($C_1$–$C_6$)-alkyl, unsubstituted or substituted by a radical chosen from halogen and O—($C_1$–$C_3$)-alkyl;
3. ($C_3$–$C_6$)-cycloalkyl;
4. ($C_1$–$C_3$)-alkyl-($C_3$–$C_6$)-cycloalkyl;
5. ($C_6$–$C_{10}$)-aryl, unsubstituted or substituted by a radical chosen from among halogen, O—($C_1$–$C_3$)-alkyl and CO—O—($C_1$–$C_3$)-alkyl; and
6. ($C_1$–$C_3$)-alkyl-($C_6$–$C_{10}$)-aryl, unsubstituted or substituted by a radical chosen from halogen and O—($C_1$–$C_3$)-alkyl;

R(3) is chosen from among
1. hydrogen;
2. COOH; and
3. COO—($C_1$–$C_4$)-alkyl;

R(4) is chosen from among
1. hydrogen;
2. halogen; and
3. ($C_1$–$C_4$)-alkyl;

R(5) is chosen from
1. hydrogen, and
2. ($C_1$–$C_4$)-alkyl;

R(6) is chosen from among 1. hydrogen;
2. $(C_1-C_4)$-alkyl;
3. $(C_1-C_3)$-alkyl-$(C_3-C_6)$-cycloalkyl; and
4. $(C_3-C_5)$-alkenyl;

X is chosen from
1. oxygen, and
2. NH;

in all the stereoisomeric forms thereof, and mixtures thereof in all ratios, and the physiologically tolerated salts thereof.

In yet another embodiment, the compounds of formula (I) include those in which

R(1) is chosen from among
1. $(C_1-C_3)$-alkyl, unsubstituted or substituted by a radical chosen from among fluorine, methoxy, ethoxy, CO—O—$(C_1-C_3)$-alkyl and $CO_2H$;
2. $(C_1-C_3)$-alkyl-cyclohexyl;
3. phenyl, substituted or unsubstituted by a radical chosen from fluorine and methoxy;
4. $(C_1-C_3)$-alkyl-phenyl, where the phenyl radical is unsubstituted or substituted by a radical chosen from fluorine and methoxy; and
5. furanyl, thienyl or pyridyl;

R(2) is chosen from among
1. hydrogen;
2. $(C_1-C_6)$-alkyl, unsubstituted or substituted by a radical chosen from among fluorine, methoxy and ethoxy;
3. phenyl, unsubstituted or substituted by a radical chosen from fluorine and methoxy; and
4. $(C_1-C_6)$-cycloalkyl;

R(4) is chosen from among
1. hydrogen;
2. methyl; and
3. chlorine;

R(5) is $(C_1-C_4)$-alkyl;
R(6) is $(C_1-C_4)$-alkyl;

and the radicals R(3) and X are as defined above, in all the stereoisomeric forms thereof, and mixtures thereof, and the physiologically tolerated salts thereof.

In an alternative embodiment, the compounds of formula (I) include those in which R(1) is chosen from among
1. $(C_1-C_3)$-alkyl, unsubstituted or substituted by a radical chosen from among fluorine, methoxy, ethoxy, CO—O—$(C_1-C_3)$-alkyl and $CO_2H$;
2. $(C_1-C_3)$-alkyl-cyclohexyl;
3. phenyl, substituted or unsubstituted by a radical chosen from fluorine and methoxy;
4. $(C_1-C_3)$-alkyl-phenyl, where the phenyl radical is unsubstituted or substituted by a radical chosen from fluorine and methoxy; and
5. furanyl, thienyl or pyridyl;

R(2) is chosen from among
1. hydrogen;
2. $(C_1-C_6)$-alkyl, unsubstituted or substituted by a radical chosen from among fluorine, methoxy and ethoxy;
3. phenyl, unsubstituted or substituted by a radical chosen from fluorine and methoxy; and
4. cyclopropyl or cyclohexyl;

R(4) is chosen from among
1. hydrogen;
2. methyl; and
3. chlorine;

R(5) is chosen from propyl and butyl, such as n-propyl, isopropyl and 2-isobutyl;
R(6) is chosen from among methyl, ethyl, n-propyl, isopropyl, n-butyl and isobutyl;

and the radicals R(3) and X are as defined above, in all the stereoisomeric forms thereof, and mixtures thereof, and the physiologically tolerated salts thereof.

In another embodiment, the compounds of formula (II):

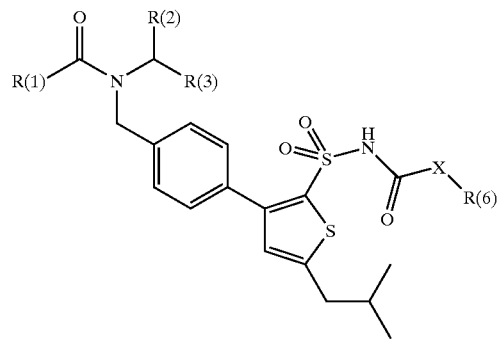

(II)

include those in which the radicals R(1), R(2), R(3), R(6) and X possess the above mentioned meanings, in all the stereoisomeric forms thereof, and mixtures thereof, and the physiologically tolerated salts thereof.

The invention furthermore relates to processes for preparing the compounds of formula (I), which processes are characterized by the reaction steps which are given below:

a) thiophene-3-boronic acids of formula (III):

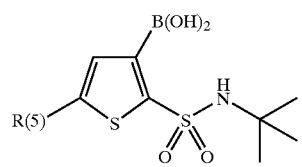

(III)

in which R(5) has the above mentioned meanings, and whose preparation is disclosed in EP-A 512 675, are reacted with p-bromobenzaldehydes of formula (IV):

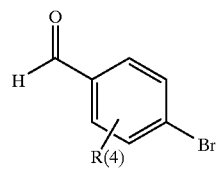

(IV)

in which R(4) is as defined above, to give compounds of formula (V):

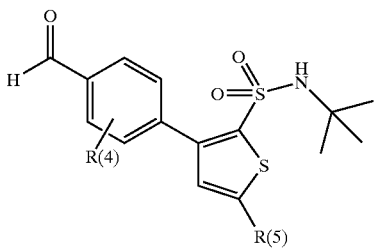

(V)

in which R(4) and (R5) have the above mentioned meanings. This Suzuki-type cross-coupling reaction may be effected using palladium(II) acetate and triphenylphosphine or tetrakis(triphenylphosphine)palladium as catalysts in the presence of a base, such as cesium carbonate or potassium carbonate, for example in solvent mixtures composed of ethanol and toluene, at temperatures up to the boiling point of the solvents; corresponding reactions are described, for example, in *Synthetic Commun.* (1981) 11:513, *J. Med. Chem.* (1995) 38:2357–2377, and *Liebigs Ann.* (1995) 1253–1257, each of which is herein incorporated by reference.

b) The compounds of formula (V) can be converted, using primary amino compounds of formula (VI),

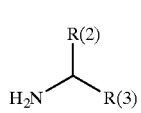

(VI)

in which R(2) and R(3) are defined as above, into compounds of formula (VII):

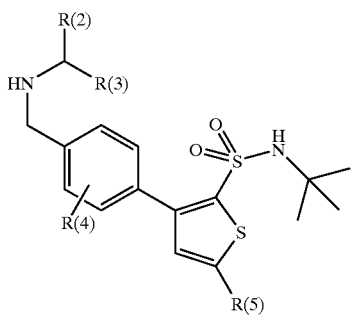

(VII)

in which the radicals R(2), R(3), R(4) and R(5) have the above mentioned meanings. This reductive amination may be effected by reacting the amines of formula (VI) with the aldehydes of formula (V) in an inert solvent, such as THF, in the presence of a reducing agent, such as sodium cyanoborohydride, and molecular sieve as a dehydrating agent, typically at room temperature or else at temperatures up to the boiling point of the solvent employed; corresponding reactions are described, for example, in *Synthesis* (1975) 135ff. As well as NaCNBH$_3$, it is also alternatively possible to use, for example, lithium aluminum hydride LiAlH$_4$, sodium borohydride NaBH$_4$, sodium triacetoxyborohydride NaBH(OAc)$_3$ or H$_2$, Pd/C as reducing agents for this amination; corresponding reactions are described, for example, in *Tetrahedron Lett.* (1987) 28:749ff, *Synthesis* (1996) 11:1325–1330, and *Tetrahedron Lett.* (1982) 23:1929ff, each of which is herein incorporated by reference.

c) Acylating the compounds of formula (VII) with acyl chlorides of the R(1)-COCl type, in which R(1) is as defined above, results in amides of formula (VIII):

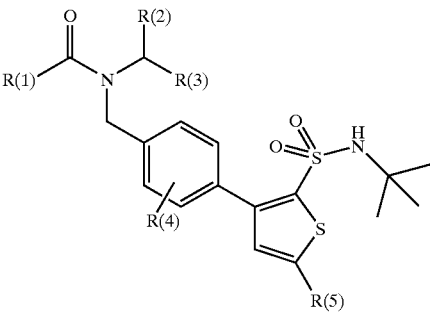

(VIII)

in which the radicals R(1), R(2), R(3), R(4) and R(5) have the above mentioned meanings. This acylation is effected, in accordance with known methods, by reacting the compounds of formula (VII) with carbonyl chlorides (which are commercially available or can be obtained from the corresponding carboxylic acids by treating them with thionyl chloride) in an inert organic solvent, such as CH$_2$Cl$_2$, which is heated to reflux, in the presence of an organic or inorganic base.

d) The compounds of formula (VIII) are converted into the sulfonamides of formula (IX):

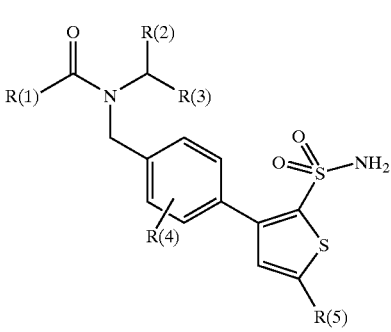

(IX)

in which R(1), R(2), R(3), R(4) and R(5) are defined as above, by eliminating the tert-butyl protecting group. This elimination may be effected by treating the compounds of formula (VIII) with organic acids, such as concentrated trifluoroacetic acid, in the presence of anisole.

e) The sulfonylurethanes of formula (Ia):

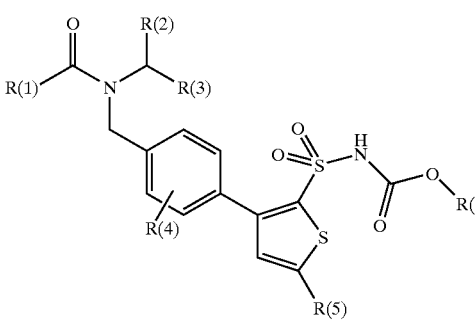

(Ia)

in which R(1), R(2), R(3), R(4), R(5), and R(6) are defined as above, can be prepared from the sulfonamides of formula (IX) by reacting the latter with R(6)-substituted chloroformic esters in which R(6) is as described above. This reaction is effected in the presence of a base, such as pyridine, and of an acylation accelerator, such as 4-pyrrolidinopyridine, at temperatures of from room temperature (RT) to 150° C., but typically at RT.

f) The sulfonylureas of formula (Ib):

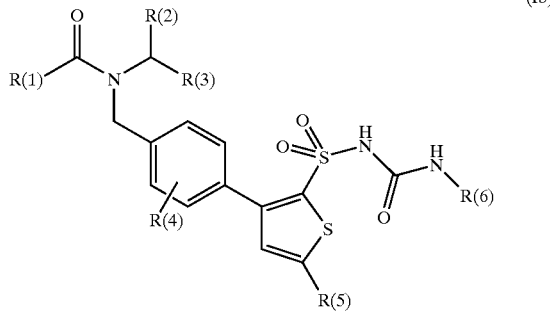

in which (R1), R(2), R(3), R(4), R(5), and R(6) are defined as above, can be obtained from the sulfonamides of formula (IX) by treating them with (R6)-substituted isocyanates in which R(6) is as described above. The reaction with the R(6)-substituted isocyanates is effected in the presence of a base in an inert solvent at temperatures of from RT to 150° C.

Examples of suitable bases include alkali metal or alkaline earth metal hydroxides, hydrides, amides or alkoxides, such as sodium hydroxide, potassium hydroxide, calcium hydroxide, sodium hydride, potassium hydride, calcium hydride, sodium amide, potassium amide, sodium methoxide, sodium ethoxide and potassium tert-butoxide. Suitable inert solvents include ethers, such as THF, dioxane, ethylene glycol dimethyl ether or diglymes; ketones, such as acetone or butanone; nitriles, such as acetonitrile; nitro compounds, such as nitromethane; esters, such as ethyl acetate; amides, such as DMF N-methylpyrrolidone, or hexamethylphosphoric triamide; sulfoxides, such as DMSO; and hydrocarbons, such as benzene, toluene or xylenes. In addition, mixtures of these solvents with each other are also suitable.

The sulfonylureas of formula (Ib) can also be prepared by reacting amines R(6)-NH$_2$ with sulfonyl isocyanate derivatives which are obtained from the sulfonamides of formula (IX), for example, by treating them with phosgene or a phosgene replacement (e.g., triphosgene) in accordance with methods which are known to the skilled person. Alternatively, the sulfonylureas of formula (Ib) can be prepared by reacting the sulfonamides of formula (IX) with 2,2,2-trichloroacetamide derivatives of a suitable amine R(6)-NH$_2$ in the presence of a base in an inert, high-boiling solvent, such as DMSO. Additionally, the sulfonylureas of formula (Ib) can be prepared from the corresponding sulfonylurethane of formula (Ia) by reaction with ethyl chloroformate, under the action of the corresponding amine R(6)-NH$_2$ in an inert, high-boiling solvent, such as toluene, at temperatures up to the boiling point of the respective solvent. Such a process is described, for example, in *J. Med. Chem.* (1995) 38:2357–2377, and in *Bioorg. Med. Chem.* (1997) 5:673–678, each of which is herein incorporated by reference. The N-unsubstituted sulfonylureas of formula (Ib), in which R(6) is hydrogen, are prepared, typically at temperatures of −10 to 0° C., by using sulfuric acid to hydrolyze the sulfonamidonitriles (which result from the reaction of the sulfonamides of formula (IX) with cyanogen bromide in the presence of K$_2$CO$_3$ in acetonitrile).

The corresponding carboxylic acids of formula (I) can then be prepared, in accordance with known methods, as are described in the literature (for example in the standard works such as Houben-Weyl, *Methoden der Organischen Chemie* [*Methods of Organic Chemistry*], Georg Thieme Verlag; Stuttgart, *Organic Reactions*, John Wiley & Sons, Inc., New York; or Larock, *Comprehensive Organic Transformations*, VCH, Weinheim) by alkaline hydrolysis of the ester groups in the compounds of formula (I).

The vascular endothelium is a metabolically active organ which has a large number of regulatory functions and which is capable of synthesizing and releasing vasoactive substances. The pathogenesis of a variety of cardiovascular diseases, such as atherosclerosis and hypertension, correlates with a dysfunction in the blood vessel-lining endothelial layer (*Eur. J. Clin. Invest.* (1993) 23:670–685). An endothelial dysfunction is characterized by a reduced synthesis and/or release of the vasorelaxing, vasoprotective and antithrombotic and antiproliferative active messengers NO and cGMP, which play an essential role in the prevention and regression of vascular remodeling and arterial hypertension. Substances which are able to stimulate the synthesis and release of these messengers are therefore potentially valuable pharmaceuticals for treating all the diseases which are characterized by an endothelial dysfunction.

A large number of published experiments have verified the fact that a breakdown product of the renin-angiotensin system, i.e. the heptapeptide angiotensin-(1–7), is a potent endogenous effector hormone of the renin-angiotensin system (*Hypertension* (1991) 18[Suppl. III]:III126–III133), the biological effect of which hormone is elicited via the stimulation of specific receptors which preferentially bind angiotensin-(1–7) (*Peptides* (1993) 14:679–684, *Hypertension* (1997) 29[part 2]:388–393)). In many cases, this effect is directed against that of the vasoconstrictor hormone angiotensin II or is opposed to this effect in a counter-regulatory manner (*Hypertension* (1997) 30[part 2]: 535–541, *Regulatory Peptides* (1998) 78:13–18).

In *Hypertension* (1992) 19[suppl. II]:II49–II55 and in *Am. J. Cardiol.* (1998) 82:17S–19S, it was demonstrated that angiotensin-(1–7) stimulates the production and/or the release of NO/cGMP and of the prostaglandins E$_2$ and I$_2$, an effect which is not blocked by pretreatment with AT$_1$ receptor and AT$_2$ receptor antagonists.

*Hypertension* (1996) 27[part 2]:523–528, reported that angiotensin-(1–7) cause an endothelial-dependent relaxation in the intact coronary arteries of dogs and pigs, while *J. Cardiovasc. Pharmacol.* (1997) 30:676–682, reported that angiotensin-(1–7) caused an endothelium-dependent relaxation of intact rat aortas which had been previously contracted with KCl, with this relaxation not being affected by AT$_1$ receptor antagonists.

*Peptides* (1993) 14:679–684 and *Am. J. Physiol.* (1995) 269:H313–H319, demonstrated that, when continuously infused through an osmotic minipump, angiotensin-(1–7) had a hypotensive effect in spontaneously hypertensive rats, with the same dose of angiotensin-(1–7) having no effect on blood pressure in normotensive rats. As a complement to these investigations, it was demonstrated, in *Hypertension* (1998) 31:699–705, that infusion of an angiotensin-(1–7) antibody increased the average arterial blood pressure in conscious, spontaneously hypertensive rats which had been pretreated with lisinopril and losartan.

In *Am. J. Hypertension* (1998) 11:137–146, it was demonstrated that the plasma levels of angiotensin-(1–7) which could be detected in humans suffering from essential hypertension were markedly lower than those which could be detected in normotensive humans.

*Hypertension* (1996) 28:104–108, showed that angiotensin-(1–7) had an anti-proliferative effect on vascular smooth muscle cells, while *Hypertension* (1999) 33[part II]:207–211, showed that angiotensin-(1–7) inhibited the proliferation of smooth muscle cells following vascular tissue damage.

In addition to this, angiotensin-(1–7) also exhibited renal effects, such as an increased natriuresis and diuresis, in sodium chloride-loaded, anesthetized normotensive Wistar rats (*Am. J. Physiol.* (1996) 270:F141–F147).

The compounds of formula (I) which are described herein are potent, nonpeptide agonists of the postulated endothelial angiotensin-(1–7) receptors. They therefore mimic the above-described biological effect, which is directed against angiotensin II, of the peptide hormone angiotensin-(1–7), which effect is to be attributed to the production and/or release of cGMP and NO from the endothelium, without, in this connection, undergoing the rapid metabolic degradation of this hormone. The described compounds of formula (I) are therefore generally suitable for treating and/or preventing diseases where the primary or secondary cause, or at least a primary or secondary component of the cause, is a reduced production and/or release of the vasorelaxing, antithrombotic and cardioprotective messengers cyclic 3',5'-guanosine monophosphate (cGMP) and nitrogen monoxide (NO). By means of stimulating the production and/or release of these vasorelaxing, antithrombotic and cardioprotective messengers, the described angiotensin-(1–7) receptor agonists of formula (I) are useful as pharmaceuticals for treating and preventing hypertension; cardiac hypertrophy; cardiac insufficiency; coronary heart diseases, such as angina pectoris; and endothelial dysfunction or endothelial damage, for example, as a consequence of atherosclerotic processes, or in connection with diabetes mellitus.

Stimulation of endothelial angiotensin-(1–7) receptors by the agonists of formula (I) causes vasodilatory and organ-protective autacoids to be released. This mechanism differs from that of angiotensin-converting enzyme (ACE) inhibition and $AT_1$ receptor blockade in that it avoids either a decrease in tissue angiotensin (ANG) II (in the case of ACE inhibitors) or effects which are associated with increased ANG II plasma values (in the case of $AT_1$ receptor antagonists) and which are currently not possible to assess.

The compounds of formula (I), and their physiologically tolerated salts, can consequently be used as pharmaceuticals in animals, such as mammals, and particularly in humans. The compounds may be provided on their own, in mixtures with each other, or together with other active compounds, in the form of pharmaceutical preparations. The present invention therefore relates to the use of compounds of formula (I), and/or their physiologically tolerated salts, for producing a medicament for treating or preventing the above mentioned syndromes, and to pharmaceutical preparations which comprise an effective dose of at least one compound of formula (I), and/or of a physiologically tolerated salt thereof, as the active constituent in addition to customary, pharmaceutically acceptable carrier substances and/or auxiliary substances. The pharmaceutical preparations can be intended for enteral or parenteral use and normally comprise from 0.5 to 90% by weight of the compound of formula (I) and/or its physiologically tolerated salts. The quantity of active compound of formula (I) and/or its physiologically tolerated salts in the pharmaceutical preparations is in general from 0.2 to 500 mg, or from 1 to 300 mg.

Pharmaceuticals which can be employed in accordance with the invention and which comprise the compounds of formula (I) and/or their physiologically tolerated salts may be administered enterally, for example orally or rectally. Such administrations may be provided, for example, in the form of pills, tablets, film tablets, sugar-coated tablets, granules, hard and soft gelatin capsules, solutions, such as aqueous, alcoholic or oily solutions, juices, drops, syrups, emulsions or suspensions. The administration can also be effected parenterally, for example subcutaneously, intramuscularly or intravenously in the form of injection solutions or infusion solutions. Examples of other suitable forms of administration include percutaneous or topical administration, for example in the form of ointments, creams, pastes, lotions, gels, sprays, powders, foams, aerosols or solutions, or use in the form of implants.

The pharmaceutical preparations which can be employed in accordance with the invention can be produced using the known standard methods for producing pharmaceutical preparations. For this, one or more compounds of formula (I) and/or their physiologically tolerated salts are brought into a suitable administration form or dosage form together with one or more solid or liquid carrier substances and/or additives or auxiliary substances. If desired, other pharmaceutically active compounds having a therapeutic or prophylactic effect may be combined in the dosage form. Such pharmaceuticals include, for example, those having cardiovascular activity, such as calcium antagonists, ACE inhibitors, AT1 receptor antagonists, NO donors, endothelin receptor antagonists, K channel openers, phosphodiesterase inhibitors, diuretics or α- and β-blockers. The administration form or dosage form can then be used as a pharmaceutical in human medicine or veterinary medicine.

Suitable carrier substances include organic or inorganic substances which are suitable for enteral (for example oral) or parenteral (for example intravenous) administration or topical uses, and which do not react with the active compounds of formula (I). Suitable carriers include, for example, water, vegetable oils, alcohols, such as ethanol, isopropanol or benzyl alcohols, 1,2-propanediol, polyethylene glycols, glycerol triacetate, gelatin, carbohydrates, such as lactose or starch, magnesium stearate, talc, lanolin, Vaseline, acetonitrile, dimethylformamide and dimethylacetamide. Pharmaceutical forms such as tablets, sugar-coated tablets, capsules, solutions, oily or aqueous solutions, syrups, juices or drops, Also, suspensions or emulsions are commonly employed for oral and rectal use. It is also possible to employ mixtures composed of two or more carrier substances. For example, mixtures may be composed of two or more solvents, such as one or more organic solvents together with water. As additives or auxiliary substances, the pharmaceutical preparations may also comprise, for example, stabilizers, wetting agents, emulsifiers, salts (e.g., to influence the osmotic pressure), glidants, preservatives, dyes, flavors and/or aromas and buffering substances. If desired, they may also comprise one or more additional active compounds, for example, one or more vitamins. The compounds of formula (I) and/or their physiologically tolerated salts can also be lyophilized and the resulting lyophilisates can, for example, be used for producing injection preparations. Liposomal preparations are also suitable for topical use.

In connection with the use according to the invention, the dose of the active compound of formula (I), and/or of a physiologically tolerated salt thereof, to be administered depends on the individual case and, as is customary, should be adjusted to the individual circumstances if an optimum effect is to be achieved. Thus, the dose typically depends on the nature and severity of the disease to be treated, the sex, age, weight and individual responsiveness of the human or animal to be treated, the strength and duration of the effect of the compounds employed, whether the therapy or prophylaxis is being performed acutely or chronically, or whether other active compounds are being administered in addition to the compounds of formula (I). In general, when treating the above mentioned syndromes in humans, a dose range of from about 0.1 mg to about 100 mg per kg per day is appropriate for achieving the sought-after effect when being administered to an adult of about 75 kg in weight. A dose range of from 1 to 20 mg per kg per day (in each case mg per kg of body weight) is typical. In this connection, the daily dose can be administered as a single dose or be divided up into several individual doses, for example one, two, three or four individual doses. The daily dose can also be administered continuously. Where appropriate, it can be necessary, depending on the individual response, to diverge, either upwards or downwards, from the specified daily dose. Pharmaceutical preparations normally comprise from 0.2 to 500 mg, or from 1 to 300 mg, of active compound of formula (I) and/or its physiologically tolerated salts.

The following assays (tests 1 and 2) demonstrate the affinity of the compounds of formula (I) for angiotensin-(1–7)-binding sites and their agonistic properties on endothelial cells:

Test 1: Binding Assay

The affinity of the compounds of formula (I) for angiotensin-(1–7) receptors was measured by means of ligand displacement experiments which were carried out on preparations of membranes obtained from primary bovine aorta endothelial cells, as are also described, for example, in *Hypertension* (1997) 29[part 2]:388–393, herein incorporated by reference.

a) Membrane Preparation:

After endothelial cells had been isolated from bovine aortas (test 1, a)), the cells were cultured in 75 cm² culture flasks (Becton Dickinson, Heidelberg) until they had reached confluence. After that, the cells were taken up with ice-cold phosphate-NaCl-EDTA buffer (50 mmol/of $NaHPO_{42}$ 0.15 mol of NaCl/L, 5 mmol of EDTA/L, pH 7.2), detached using a rubber scraper and centrifuged (1500×g, 5 min). The resulting cell pellet was frozen (–80° C.) for subsequent membrane preparation.

The thawed cell pellet was homogenized in ice-cold phosphate-NaCl-EDTA buffer (glass/teflon Potter, 1000 rpm, 10 strokes). The membranes were isolated by subsequently centrifuging (30 000×g, 20 min) the cell homogenate. The cell pellet which was obtained in this way was resuspended in modified HEPES buffer (10 nmol of HEPES/L, 0.1 mol of NaCl/L, 5 mmol of $MgCl_2$/L, pH 7.4) in the added presence of 0.2% bovine serum albumin and a cocktail of protease inhibitors (Complete™, Boehringer Mannheim). After a protein determination had been subsequently carried out on the membrane suspension (using the Lowry method), the suspension was immediately used for the ligand binding experiment.

b) Binding Experiments:

The experiments were carried out on 96-well Opak plates, which are equipped with Durapore filters (0.65 µm pore size; Millipore, Eschborn). Before beginning the experiment, the filters were pretreated for 30 min with 1% bovine serum albumin in order to minimize nonspecific binding of the radioactive ligand and the cold substances to the filter material. The incubation was carried out in a total volume of 200 µl: 50 µl of $^{125}$I-ANG-(1–7), 20 µl of cold, nonradioactive ANG-(1–7) or test substances of formula (I), 30 µl of buffer and 100 µl of membranes (20 µg of protein). The binding reaction was started by adding the radioactive ligand. The samples were incubated at room temperature for 45 min while being continuously shaken. The binding reaction was terminated by means of vacuum filtration (–20 kPa vacuum; Multiscreen filtration system, Millipore, Eschborn). In order to completely remove the free radioactivity, which was not membrane-bound, the filters were washed twice under vacuum with 250 µl of ice-cold phosphate-NaCl-EDTA buffer (50 mmol of $NaHPO_4$/L, 0.15 mol of NaCl/L, 5 mmol/L EDTA, pH 7.2) and then dried. The radioactive content on the dried filters was determined using a gamma counter.

For the competition experiments (determination of "individual values" or $IC_{50}$ values), a concentration of from 7.5 to 10 nmol of $^{125}$I-ANG-(1–7)/L (specific activity, 1500–2100 mCi/mg) was employed, with and without increasing concentrations of the test substances of formula (I). The nonspecific binding was in each case measured in the presence of 10 µmol of nonradioactive ANG-(1–7)/L.

c) Results:

| Example | $IC_{50}$ |
|---|---|
| 4 | 21 nM |
| 9 | 30 nM |

These values, which are listed by way of example, for the compounds of Examples 4 and 9, infra, demonstrate the high affinity of compounds of formula (I) for angiotensin-(1–7) receptors on endothelial cells. In this connection, the compounds of formula (I) exhibit no affinity, or only a negligible ($>10^{-6}$ M) affinity, for ANG II receptors of the $AT_1$ and $AT_2$ types.

Test 2: Functional Assay:

The stimulatory effect of the compounds of formula (I) on the production of intracellular cGMP, which is a marker for the production and release of NO in endothelial cells, was measured on primarily cultivated endothelial cells derived from bovine aortas, as described, for example, in *J. Pharmacol. Exp. Ther.* (1992) 262:729–733, herein incorporated by reference.

a) Cell Cultures:

After having been enzymatically digested (dispase II; Boehringer, Mannheim) from the bovine aorta, the endothelial cells were taken up in culture medium (Dulbecco's modified Eagle's Ham's F 12 medium 1:1 containing penicillin (10 U/L), streptomycin (10 ug/L), L-glutamine (1 mmol/L), glutathione and L-(+)-ascorbic acid (in each case 5 mg/L) and heat-inactivated fetal calf serum (20%)), washed once (centrifugation at 170×g, 10 min) and resuspended in culture medium. This cell suspension was seeded in 6-well plates (Nunc Intermed, Wiesbaden) (~250 µg of protein or $3\times10^{-5}$ cells per well), with the wells then being filled with culture medium and the plates kept at 37° C. in an incubator which was moistened and gassed with 95% $O_2$-5% $CO_2$.

b) cGMP Determinations:

After confluence had been reached (6–8 days after seeding), the culture medium was removed and the cell monolayer was washed twice with warm HEPES/Tyrode's solution. After that, the cells were preincubated, at 37° C. for 15 min, in HEPES/Tyrode's solution containing IBMX (3-isobutyl-1-methylxanthine, $10^{-4}$ mol/L, Serva, Heidelberg). The incubation was started by adding SOD (bovine erythrocyte superoxide dismutase, $3\times10^{-7}$ mol/L, Serva, Heidelberg) and the test substances of formula (I) at the given concentrations. After the appropriate incubation time, the incubation medium was aspirated and the cells which remained behind were immediately extracted in 1 N formic acid/acetone (v/v, 15:85) and scraped off. The resulting suspension was ultrasonicated (10 sec) and then centrifuged down (3000×g, 10 min). For the purpose of determining cGMP by means of radioimmunoassay (New England Nuclear, Boston, Mass.), the supernatant was lyophilized and the lyophilisate taken up in sodium acetate buffer (0.05 mol/L; pH 6.2). The content (pmol) of intracellular cGMP was related to mg of cell protein.

c) Results:

| Example | $EC_{50}$ |
|---------|-----------|
| 4 | $6.0 \times 10^{-7}$ M |
| 9 | $0.4 \times 10^{-7}$ M |

The listed values for the compounds described in Examples 4 and 9, infra, which compounds are taken as being representative of the claimed compounds, demonstrate the agonistic effect of the compounds of formula (I) on angiotensin-(1–7) receptors.

At the same time, this effect of the compounds from Examples 4 and 9, infra, on the production of cGMP, as a marker for the synthesis and release of NO, is not influenced by preincubation with an angiotensin II receptor antagonist of either the $AT_1$ subtype, such as EXP3174, or of the $AT_2$ subtype, such as PD 123,319. By contrast, the stimulatory effect of the compounds from Examples 4 and 9 on cGMP is inhibited by preincubation with a selective antagonist of the angiotensin-(1–7) receptors, i.e. [D-Ala$^7$]-angiotensin-(1–7), which is described, for example, in *Brain Res. Bull.* (1994) 35:293–298, herein incorporated by reference, thereby demonstrating the specificity of this functional effect.

LIST OF ABBREVIATIONS abs. absolute
cGMP cyclic guanosine monophosphate
$CH_2Cl_2$ dichloromethane
DCI desorption chemical ionization
DMF N,N-dimethylformamide
EA ethyl acetate
ESI electron spray ionization
FAB fast atom bombardment
M.p. melting point
M.S. mass spectrometry
sat. saturated
h hour(s)
min. minute(s)
NO nitrogen monoxide
RT room temperature
THF tetrahydrofuran The invention is clarified by the following examples, without being restricted to these examples.

EXAMPLE 1

Methyl 2-N-benzoyl-2-N-[4-[2-(n-butyloxycarbonylsulfonamido)-5-isobutyl-3-thienyl]benzyl]amino-3-methyl-L-butyrate

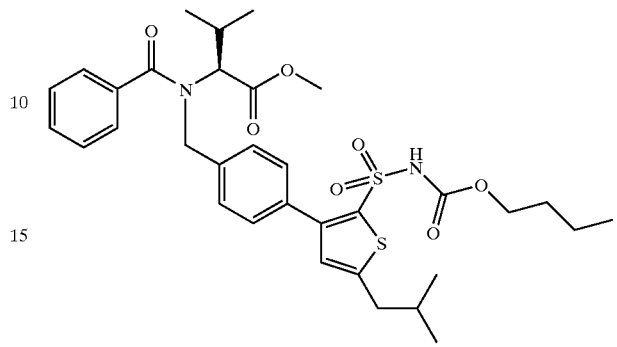

a) 2-(N-tert-Butyl)sulfonamidothiophene 85.5 ml (0.82 mol) of N-tert-butylamine were slowly added dropwise, while cooling with ice, to a solution of 50 g (0.27 mol) of 2-thiophenesulfonyl chloride in 500 ml of $CH_2Cl_2$, and the resulting solution was stirred at RT for 1 h. 500 ml of 1N hydrochloric acid were subsequently added to the reaction solution, after which the organic phase was separated off and washed with water. After drying over $Na_2SO_4$, stripping off the solvent, and drying under high vacuum, 58.2 g of the title compound finally resulted in the form of a pale yellow oil.

$R_f$ ($SiO_2$, EA/n-heptane 1:1)=0.39
MS (ESI): m/z=220 [M+H]$^+$ b) 5-Isobutyl-2-[(N-tert-butyl)sulfonamido]thiophene 173.2 ml (0.27 mol) of a 15% solution of n-butyllithium in hexane were added dropwise, in an argon atmosphere, to a solution of 24.2 g (0.11 mol) of the compound from example 1a) in 450 ml of abs. THF, which had been cooled to −78 C, and the resulting solution was stirred at −20 C for 3 h and then at RT for 2 h. The solution was cooled down once again to −20 C, and 15 ml (0.13 mol) of 1-iodo-2-methylpropane were added at this temperature. After having been stirred at 0 C for 1 h, the reaction solution was left to stand overnight. 150 ml of sat. ammonium chloride solution were then added and, after 150 ml of water had been added, the whole solution was extracted several times with EA. The combined EA phases were dried over $Na_2SO_4$ and concentrated. The residue which remained was purified by chromatography on $SiO_2$ using EA/n-heptane (1:6) as the eluent, with 9.8 g of the title compound being obtained in the form of a brown oil.

$R_f$ ($SiO_2$, EA/n-heptane 1:4)=0.28
MS (ESI): m/z=276 [M+H]$^+$ c) 5-Isobutyl-2-[(N-tert-butyl)sulfonamido]thiophene-3-boronic acid 54.4 ml of a 15% solution of n-butyllithium in hexane were added slowly dropwise, in an argon atmosphere, to a solution of 9.6 g (35.1 mmol) of the compound from example 1b) in 350 ml of abs. THF, which had been cooled down to −78 C, and the resulting solution was heated, while stirring, to RT within the space of 2 h. After the solution had been subsequently cooled down to 0 C, 8.93 ml (52.2 mmol) of trimethyl borate were added and the resulting reaction solution was stirred, first at 0 C for 1 h and then at RT for 24 h. After 70 ml of 2N hydrochloric acid had been added and the mixture had been stirred at RT for 30 min, the organic phase was separated off, washed with water and dried over $Na_2SO_4$; the solvent was then removed in a vacuum. Chromatographic purification of the remaining residue on $SiO_2$ using $CH_2Cl_2$/methanol (30:1) as the eluent yielded 10.3 g of the title compound in the form of a pale brown oil.

$R_f$ ($SiO_2$, EA/n-heptane 1:1)=0.22

MS (ESI): m/z=320 [M+H]$^+$ d) 4-[5-Isobutyl-2-[(N-tert-butyl)sulfonamido]-3-thienyl]benzaldehyde In an argon atmosphere, a solution of 3.72 g (14.5 mmol) of the compound from example 1c) in 75 ml of ethanol was added slowly to a solution of 2.68 g (14.5 mmol) of 4-bromobenzaldehyde and 460 mg (0.40 mmol) of tetrakis(triphenylphosphine) palladium-(0) in 75 ml of toluene, and the mixture was stirred at RT for 15 min. After 16.9 ml of a 2N solution of $Cs_2CO_3$ had been added, the resulting reaction solution was heated at reflux for 3 h. It was subsequently concentrated down to dryness and the residue which remained was taken up in EA; the EA solution was washed with water and concentrated after having been dried over $Na_2SO_4$. Chromatographic purification of the remaining residue on $SiO_2$ using EA/n-heptane (1:4) as the eluent yielded 5.46 g of the title compound as a slightly yellow-colored solid.

M.p.: 140–143° C.

$R_f$ ($SiO_2$, EA/n-heptane 1:2)=0.47

MS (FAB): m/z=380 [M+H]$^+$ e) Methyl 2-N-[4-[2-(N-tert-butyl)sulfonamido-5-isobutyl-3-thienyl]benzyl]amino-3-methyl-L-butyrate In an argon atmosphere, 5.40 g (14.4 mmol) of the compound from example 1d) were dissolved in 160 ml of abs. THF, and 16 g of activated molecular sieve (5 Angström) and 4.82 g (28.8 mmol) of L-valine methyl ester hydrochloride were then added to this solution. After this reaction mixture had been stirred at RT for 30 min, a solution of 910 mg (14.4 mmol) of sodium cyanoborohydride in 18 ml of methanol was slowly added to it dropwise, at 0–5° C., and the mixture was subsequently stirred at RT overnight. After filtering, the resulting solution was concentrated and the residue which remained was purified by chromatography on $SiO_2$ using EA/n-heptane (1:2) as the eluent. Combining the product-containing fractions and concentrating them yielded 4.41 g of the title compound in the form of an amorphous solid.

$R_f$ ($SiO_2$, EA/n-heptane 1:4)=0.43

MS (ESI): m/z=495 [M+H]$^+$ f) Methyl 2-N-benzoyl-2-N-[4-[2-(N-tert-butyl)sulfonamido-5-isobutyl-3-thienyl]benzyl]amino-3-methyl-L-butyrate In an argon atmosphere, a solution of 1.0 g (2.02 mmol) of the compound from example 1e), 352 µl (3.03 mmol) of benzoyl chloride and 280 µl (2.02 mmol) of triethylamine in 20 ml of $CH_2Cl_2$ was heated at reflux for 1 h. Subsequently, the solution was washed with water and the organic phase was dried over $Na_2SO_4$, filtered and concentrated. Chromatographic purification of the remaining residue on $SiO_2$ using EA/n-heptane (1:2) as the eluent yielded 1.20 g of the title compound as an amorphous solid.

$R_f$ ($SiO_2$, EA/n-heptane 1:4)=0.12

MS (ESI): m/z=599 [M+H]$^+$ g) Methyl 2-N-benzoyl-2-N-[4-[2-sulfonamido-5-isobutyl-3-thienyl]benzyl]amino-3-methyl-L-butyrate A solution of 1.15 g (1.92 mmol) of the compound from example 1f), 2.35 ml (21.5 mmol) of anisole and 12.2 ml of trifluoroacetic acid was stirred at RT for a period of 24 h. The reaction solution was concentrated and the residue was taken up in EA. The EA solution was then washed with water and sat. sodium chloride solution, dried over $Na_2SO_4$ and concentrated. After the resulting residue had been purified by chromatography on $SiO_2$ using EA/n-heptane (1:2) as the eluent, 834 mg of the title compound resulted in the form of a white solid.

M.p.: 50° C. (softening)

$R_f$ ($SiO_2$, EA/n-heptane 1:2)=0.28

MS (ESI): m/z=543 [M+H]$^+$ h) Methyl 2-N-benzoyl-2-N-[4-[2-(n-butyloxycarbonylsulfonamido)-5-isobutyl-3-thienyl]benzyl]amino-3-methyl-L-butyrate Under an argon atmosphere, a solution of 400 mg (0.74 mmol) of the compound from example 1g), 13 mg (0.09 mmol) of 4-pyrrolidinopyridine and 927 µl (7.37 mmol) of n-butyl chloroformate in 6 ml of abs. pyridine was stirred at RT over a period of 2 days. The reaction solution was subsequently concentrated to dryness in a vacuum and the residue was taken up in $CH_2Cl_2$. The resulting solution was washed consecutively with a 10% solution of citric acid and with water, dried over $Na_2SO_4$ and concentrated. Purification of the remaining residue by chromatography on $SiO_2$ using $CH_2Cl_2$/methanol (20:1) yielded 470 mg of the title compound in the form of a slightly yellow amorphous foam.

$R_f$ ($SiO_2$, EA/n-heptane 1:1)=0.35

MS (ESI): m/z=643 [M+H]$^+$

EXAMPLE 2

Ethyl 2-N-benzoyl-2-N-[4-[2-(n-butyloxycarbonylsulfonamido)-5-isobutyl-3-thienyl]benzyl]amino-3-methyl-L-butyrate Ethyl 2-N-[4-[2-(N-tert-butyl)sulfonamido-5-isobutyl-3-thienyl]benzyl]amino-3-methyl-L-butyrate The title compound was prepared by reacting the compound from example 1d) with L-valine ethyl ester using the method given in example 1e). When this was done, 600 mg (1.58 mmol) of the compound from example 1d) and 574 mg (3.16 mmol) of L-valine ethyl ester gave rise to 430 mg of the desired title compound in the form of a slightly yellow-colored oil.

$R_f$ ($SiO_2$, EA/n-heptane 1:4)=0.11

MS (ESI): m/z=509 [M+H]$^+$ b) Ethyl 2-N-benzoyl-2-N-[4-[2-(N-tert-butyl)sulfonamido-5-isobutyl-3-thienyl]benzyl]amino-3-methyl-L-butyrate The title compound was prepared by reacting the compound from example 2a) with benzoyl chloride using the method given in example 1f). When this was done, 215 mg (0.42 mmol) of the compound from example 2a) and 73.7 μl (0.63 mmol) of benzoyl chloride gave rise to 218 mg of the desired title compound in the form of a white amorphous foam.

$R_f$ (SiO$_2$, EA/n-heptane 1:1)=0.44

MS (ESI): m/z=613 [M+H]$^+$ c) Ethyl 2-N-benzoyl-2-N-[4-[2-sulfonamido-5-isobutyl-3-thienyl]benzyl]amino-3-methyl-L-butyrate The title compound was prepared by treating the compound from example 2b) with trifluoroacetic acid using the method given in example 1g). When this was done, 212 mg (0.35 mmol) of the compound from example 2b) gave rise to 161 mg of the desired title compound in the form of a white amorphous foam.

$R_f$ (SiO$_2$, EA/n-heptane 1:1)=0.35

MS (ESI): m/z=557 [M+H]$^+$ d) Ethyl 2-N-benzoyl-2-N-[4-[2-(n-butyloxycarbonylsulfonamido)-5-isobutyl-3-thienyl]benzyl]amino-3-methyl-L-butyrate The title compound was prepared by reacting the compound from example 2c) with n-butyl chloroformate using the method given in example 1h). When this was done, 80 mg (0.14 mmol) of the compound from example 2c) and 180.6 μl (1.44 mmol) of n-butyl chloroformate gave rise to 69 mg of the desired title compound in the form of a white amorphous foam.

$R_f$ (SiO$_2$, EA/n-heptane 1:1)=0.29

MS (ESI): m/z=657 [M+H]$^+$

EXAMPLE 3

2-N-Benzoyl-2-N-[4-[2-(n-butyloxycarbonylsulfonamido)-5-isobutyl-3-thienyl]benzyl]amino-3-methyl-L-butyric acid

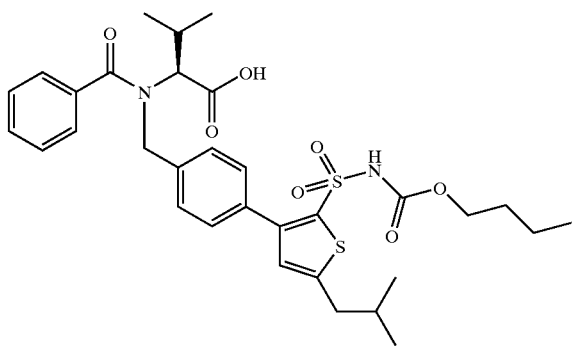

A solution composed of 358 mg (0.56 mmol) of the compound from example 1h) and 3.7 ml of 2N sodium hydroxide solution was stirred at RT for 3 days. The reaction solution was subsequently concentrated and the pH of the remaining solution was adjusted to 6 by adding 2N hydrochloric acid. The precipitate which settled out was filtered off with suction, washed with a little water and dried under high vacuum. This resulted in 173 mg of the title compound in the form of a white amorphous solid.

$R_f$ (SiO$_2$, EA/n-heptane 2:1)=0.12

MS (FAB): m/z=629 [M+H]$^+$

EXAMPLE 4

Methyl 2-N-benzoyl-2-N-[4-[2-(ethylaminocarbonylsulfonamido)-5-isobutyl-3-thienyl]benzyl]amino-3-methyl-L-butyrate

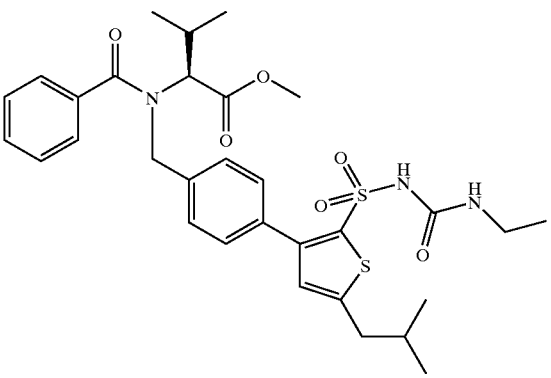

A solution of 392 mg (0.72 mmol) of the compound from example 1g), 228 mg (1.64 mmol) of K$_2$CO$_3$ and 57.2 μl (0.72 mmol) of ethyl isocyanate in 5 ml of abs. DMF was stirred at reflux for 2 h. 26 ml of a 10% solution of K$_2$HPO$_4$ was subsequently added to the reaction solution, which was then extracted several times with EA. The EA extracts were combined, dried over Na$_2$SO$_4$ and concentrated to dryness in a vacuum. Chromatographic purification of the remaining residue on SiO$_2$ using CH$_2$Cl$_2$/methanol (40:1) as the eluent yielded 362 mg of the title compound in the form of a white solid.

M.p.: 65° C. (softening)

$R_f$ (SiO$_2$, EA/n-heptane 1:1)=0.31

MS (ESI): m/z=614 [M+H]$^+$

EXAMPLE 5

Ethyl 2-N-benzoyl-2-N-[4-[2-(ethylaminocarbonylsulfonamido)-5-isobutyl-3-thienyl]benzyl]amino-3-methyl-L-butyrate

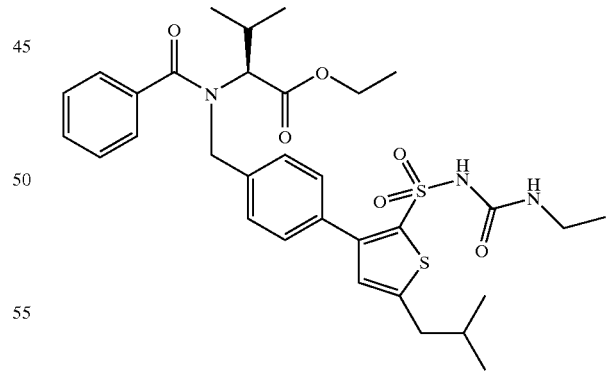

The title compound was prepared by reacting the compound from example 2c) with ethyl isocyanate using the method given in example 4). When this was done, 80 mg (0.14 mmol) of the compound from example 2c) and 11.3 μl (0.14 mmol) of ethyl isocyanate gave rise to 89 mg of the desired title compound in the form of a white solid.

M.p.: 88–90° C.

$R_f$ (SiO$_2$, EA/n-heptane 1:1)=0.12

MS (ESI): m/z=628 [M+H]+

EXAMPLE 6

2-N-Benzoyl-2-N-[4-[2-(ethylaminocarbonylsulfonamido)-5-isobutyl-3-thienyl]benzyl]amino-3-methyl-L-butyric acid

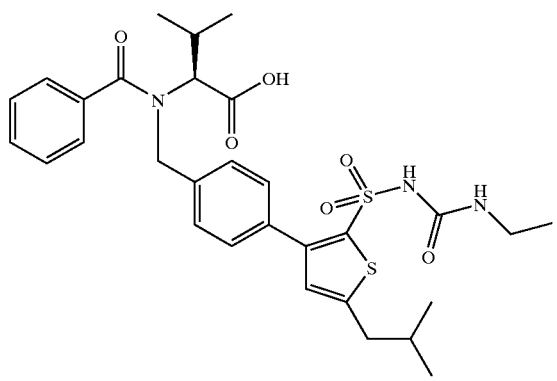

A solution composed of 80 mg (0.13 mmol) of the compound from example 1h) and 1 ml of/6N sodium hydroxide solution was stirred at RT for 3 days. The reaction solution was subsequently concentrated and the pH of the remaining solution was adjusted to 6 by adding 2 N hydrochloric acid. The precipitate which settled out was filtered off with suction, washed with a little water and dried under high vacuum. This resulted in 69 mg of the title compound in the form of a white solid.

M.p.: 149° C.
$R_f$ (SiO$_2$, EA/n-heptane 1:2)=0.12
MS (ESI): m/z=600 [M+H]+

EXAMPLE 7

Methyl 2-N-acetyl-2-N-[4-[2-(n-butyloxycarbonylsulfonamido)-5-isobutyl-3-thienyl]benzyl]amino-3-methyl-L-butyrate

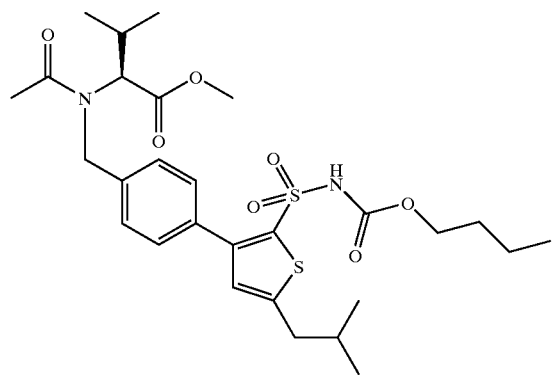

a) Methyl 2-N-acetyl-2-N-[4-[2-(N-tert-butyl)sulfonamido-5-isobutyl-3-thienyl]benzyl]amino-3-methyl-L-butyrate Under an argon atmosphere, a solution of 1.0 g (2.02 mmol) of the compound from example 1e), 280 μl (2.02 mmol) of triethylamine and 216 μl (3.03 mmol) of acetyl chloride in 20 ml of CH$_2$Cl$_2$ was stirred at reflux for 3 h. The reaction solution was subsequently washed with water, dried over Na$_2$SO$_4$ and concentrated to dryness in a vacuum. Chromatographic purification of the remaining residue on SiO$_2$ using EA/n-heptane (1:2) as the eluent yielded 854 mg of the title compound in the form of a white amorphous foam.

$R_f$ (SiO$_2$, EA/n-heptane 1:2)=0.17
MS (ESI): m/z=537 [M+H]+ b) Methyl 2-N-acetyl-2-N-[4-[2-sulfonamido-5-isobutyl-3-thienyl]benzyl]amino-3-methyl-L-butyrate The title compound was prepared by treating the compound from example 7a) with trifluoroacetic acid using the method given in Example 1g). When this was done, 819 mg (1.53 mmol) of the compound from example 7a) gave rise to 510 mg of the desired title compound in the form of a white solid.

M.p.: 163–165 ° C.
$R_f$ (SiO$_2$, EA/n-heptane 1:2)=0.10
MS (ESI): m/z=481 [M+H]+ c) Methyl 2-N-acetyl-2-N-[4-[2-(n-butyloxycarbonylsulfonamido)-5-isobutyl-3-thienyl]benzyl]amino-3-methyl-L-butyrate The title compound was prepared by reacting the compound from example 7b) with n-butyl chloroformate using the method given in example 1h). When this was done, 240 mg (0.50 mmol) of the compound from example 7b) and 628 μl (5.00 mmol) of n-butyl chloroformate gave rise to 270 mg of the desired title compound in the form of a white amorphous solid.

$R_f$ (SiO$_2$, EA/n-heptane 1:1)=0.07
MS (ESI): m/z=581 [M+H]+

EXAMPLE 8

2-N-Acetyl-2-N-[4-[2-(n-butyloxycarbonylsulfonamido)-5-isobutyl-3-thienyl]benzyl]amino-3-methyl-L-butyric acid

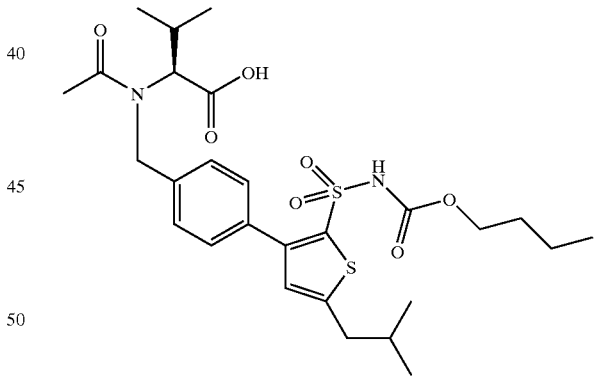

The title compound was prepared by alkaline hydrolysis of the compound from example 7c), by treating it with sodium hydroxide solution using the method given in example 3. When this was done, 174 mg (0.30 mmol) of the compound from example 7c) gave rise to 147 mg of the desired title compound in the form of a white amorphous solid.

$R_f$ (SiO$_2$, EA/n-heptane 2:1)=0.07
MS (FAB): m/z=567 [M+H]+

EXAMPLE 9

Methyl 2-N-acetyl-2-N-[4-[2-(ethylaminocarbonylsulfonamido)-5-isobutyl-3-thienyl]

benzyl]amino-3-methyl-L-butyrate

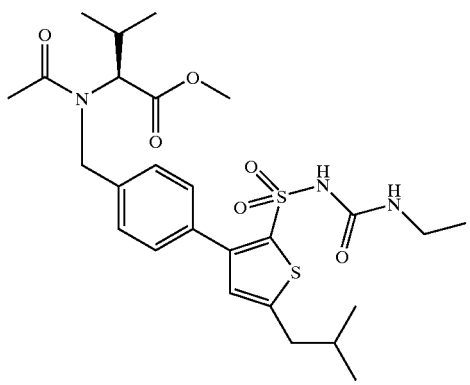

The title compound was prepared by reacting the compound from example 7b) with ethyl isocyanate using the method given in example 4). When this was done, 234 mg (0.49 mmol) of the compound from example 7b) gave rise to 245 mg of the title compound in the form of a white solid.
M.p.: 130° C.
$R_f$ (SiO$_2$, EA/n-heptane 1:1)=0.11
MS (ESI): m/z=552 [M+H]$^+$

EXAMPLE 10

Ethyl 2-N-acetyl-2-N-[4-[2-(ethylaminocarbonylsulfonamido)-5-isobutyl-3-thienyl]benzyl]amino-3-methyl-L-butyrate

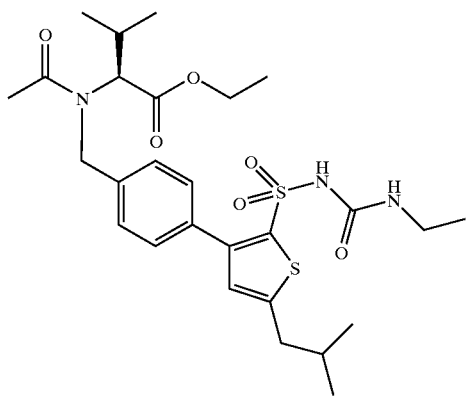

Ethyl 2-N-acetyl-2-N-[4-[2-(N-tert-butyl)sulfonamido-5-isobutyl-3-thienyl]benzyl]amino-3-methyl-L-butyrate The title compound was prepared by reacting the compound from example 2a) with acetyl chloride using the method given in example 7a). When this was done, 215 mg (0.42 mmol) of the compound from example 2a) gave rise to 113 mg of the title compound in the form of a pale yellow oil.
$R_f$ (SiO$_2$, EA/n-heptane 1:2)=0.26
MS (ESI): m/z=551 [M+H]$^+$ b) Ethyl 2-N-acetyl-2-N-[4-[2-sulfonamido-5-isobutyl-3-thienyl]benzyl]amino-3-methyl-L-butyrate The title compound was prepared by treating the compound from example 10a) with trifluoroacetic acid using the method given in example 1g). When this was done, 110 mg (0.20 mmol) of the compound from example 10a) gave rise to 74 mg of the title compound in the form of a white amorphous foam.

$R_f$ (SiO$_2$, EA/n-heptane 1:1)=0.17
MS (ESI): m/z=495 [M+H]$^+$ c) Ethyl 2-N-acetyl-2-N-[4-[2-(ethylaminocarbonylsulfonamido)-5-isobutyl-3-thienyl]benzyl]amino-3-methyl-L-butyrate The title compound was prepared by reacting the compound from example 10b) with ethyl isocyanate using the method given in example 4). When this was done, 71 mg (0.14 mmol) of the compound from example 10b) gave rise to 52 mg of the title compound in the form of a white solid.
M.p.: 81° C.
$R_f$ (SiO$_2$, EA/n-heptane 1:1)=0.06
MS (ESI): m/z=566 [M+H]$^+$

EXAMPLE 11

2-N-Acetyl-2-N-[4-[2-(ethylaminocarbonylsulfonamido)-5-isobutyl-3-thienyl]benzyl]amino-3-methyl-L-butyric acid

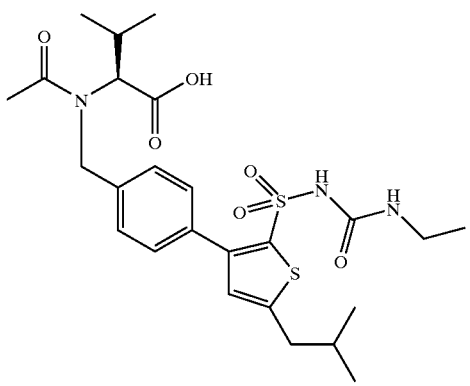

The title compound was prepared by treating the compound from example 9) with sodium hydroxide solution using the method given in example 6). When this was done, 60 mg (0.11 mmol) of the compound from example 9) gave rise to 40 mg of the desired title compound in the form of a white solid.
M.p.: 136° C.
$R_f$ (SiO$_2$, EA/n-heptane. 2:1)=0.05
MS (ESI): m/z=538 [M+H]$^+$

EXAMPLE 12

Methyl 2-N-(2-furanoyl)-2-N-[4-[2-(n-butyloxycarbonylsulfonamido)-5-isobutyl-3-thienyl]benzyl]amino-3-methyl-L-butyrate

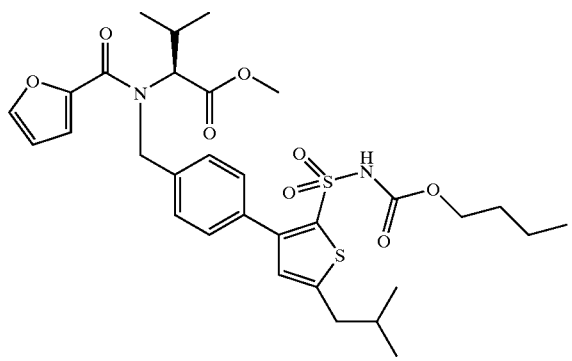

Methyl 2-N-(2-furanoyl)-2-N-[4-[2-(N-tert-butyl)sulfonamido-5-isobutyl-3-thienyl]benzyl]amino-3-methyl-L-butyrate In an argon atmosphere, a solution of 750 mg (1.52 mmol) of the compound from example 1e), 224 μl (2.27 mmol) of furan-2-carbonyl chloride and 210 μl (1.52 mmol) of triethylamine in 18 ml of $CH_2Cl_2$ was heated at reflux for 4 h. Subsequently, water was added to the reaction solution and the organic phase was separated off, dried over $Na_2SO_4$ and concentrated to dryness in a vacuum. Purification of the residue which remained by chromatography on $SiO_2$ using EA/n-heptane (1:3) as the eluent yielded 870 mg of the title compound as a white solid.
M.p.: 59° C.
$R_f$ ($SiO_2$, EA/n-heptane 1:1)=0.36
MS (ESI): m/z=589 [M+H]$^+$ b) Methyl 2-N-(2-furanoyl)-2-N-[4-[2-sulfonamido-5-isobutyl-3-thienyl]benzyl]amino-3-methyl-L-butyrate The title compound was prepared by treating the compound from example 12a) with trifluoroacetic acid using the method given in example 1g). When this was done, 860 mg (1.47 mmol) of the compound from example 12a) gave rise to 487 mg of the desired title compound in the form of a white solid.
M.p.: 57° C.
$R_f$ ($SiO_2$, EA/n-heptane 2:1)=0.28
MS (ESI): m/z =533 [M+H]$^+$ c) Methyl 2-N-(2-furanoyl)-2-N-[4-[2-(n-butyloxycarbonylsulfonamido)-5-isobutyl-3-thienyl]benzyl]amino-3-methyl-L-butyrate The title compound was prepared by reacting the compound from example 12b) with n-butyl chloroformate using the method given in example 1h). When this was done, 227 mg (0.43 mmol) of the compound from example 12b) and 538 μl (4.27 mmol) of n-butyl chloroformate gave rise to 270 mg of the desired title compound in the form of a pale yellow amorphous foam.
$R_f$ ($SiO_2$, EA/n-heptane 1:1)=0.14
MS (ESI): m/z=633 [M+H]$^+$

EXAMPLE 13

2-N-(2-Furanoyl)-2-N-[4-[2-(n-butyloxycarbonylsulfonamido)-5-isobutyl-3-thienyl]benzyl]amino-3-methyl-L-butyric acid

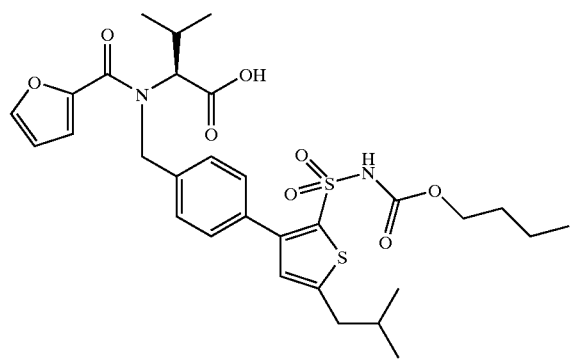

The title compound was prepared by treating the compound from example 12c) with sodium hydroxide solution using the method given in example 6). When this was done, 140 mg (0.22 mmol) of the compound from example 12c) gave rise to 122 mg of the desired title compound in the form of a white solid.
M.p.: 93° C.
$R_f$ ($SiO_2$, $CH_2Cl_2$/methanol 18:2)=0.23
MS (ESI): m/z=619 [M+H]$^+$

EXAMPLE 14

Methyl 2-N-(2-furanoyl)-2-N-[4-[2-(methylaminocarbonylsulfonamido)-5-isobutyl-3-thienyl]benzyl]amino-3-methyl-L-butyrate

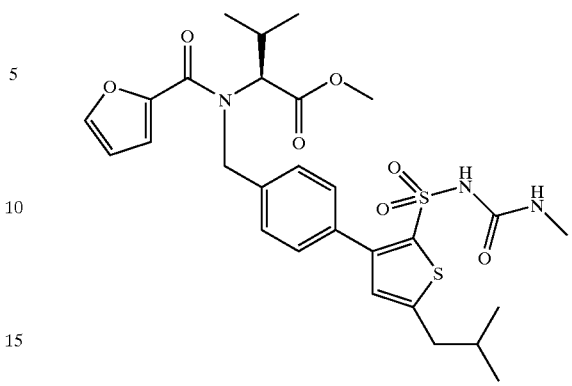

83.6 mg (0.47 mmol) of N-methyl-2,2,2-trichloroacetamide and 52.6 mg (1.30 mmol) of powdered NaOH were added to a solution of 230 mg (0.43 mmol) of the compound from example 12b) in 4 mL of DMSO, and the mixture was stirred at 80° C. for 1.5 h. The reaction solution was cooled down, after which ice was added and the pH was adjusted to 4 by adding 2 N hydrochloric acid. The precipitate which settled out in this connection was filtered off with suction, washed with water, dried and purified by chromatography on $SiO_2$ using EA/heptane (4:1) as the eluent. 210 mg of the title compound were obtained in the form of a white solid.
M.p.: 84° C.
$R_f$ ($SiO_2$, EA/n-heptane 4:1)=0.12
MS (FAB): m/z=590 [M+H]$^+$

EXAMPLE 15

2-N-(2-Furanoyl)-2-N-[4-[2-(methylaminocarbonylsulfonamido)-5-isobutyl-3-thienyl]benzyl]amino-3-methyl-L-butyric acid

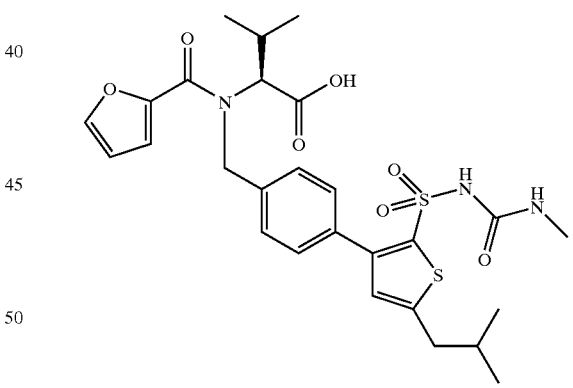

The title compound was prepared by treating the compound from example 14) with sodium hydroxide solution using the method given in example 6). When this was done, 150 mg (0.25 mmol) of the compound from example 14) gave rise to 136 mg of the desired title compound in the form of a white solid.
M.p.: 134° C.
$R_f$ ($SiO_2$, EA/n-heptane 1:1)=0.14
MS (FAB): m/z=576 [M+H]$^+$

EXAMPLE 16

Methyl 2-N-(3-methoxycarbonylpropionyl)-2-N-[4-[2-(n-butyloxycarbonylsulfonamido)-5-isobutyl-3-thienyl]

benzyl]amino-3-methyl-L-butyrate

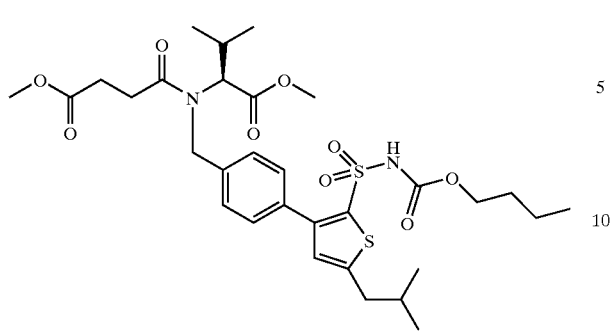

Methyl 2-N-(3-methoxycarbonylpropionyl)-2-N-[4-[2-(N-tert-butyl)sulfonamido-5-isobutyl-3-thienyl]benzyl]amino-3-methyl-L-butyrate The title compound was prepared by reacting the compound from example 1e) with 3-carbomethoxypropionyl chloride using the method given in example 1f). When this was done, 750 mg (1.52 mmol) of the compound from example 1e) gave rise to 904 mg of the desired title compound as a pale yellow oil.

$R_f$ (SiO$_2$, EA/n-heptane 1:3)=0.18

MS (ESI): m/z=609 [M+H]$^+$ b) Methyl 2-N-(3-methoxycarbonylpropionyl)-2-N-[4-[2-sulfonamido-5-isobutyl-3-thienyl]benzyl]amino-3-methyl-L-butyrate The title compound was prepared by treating the compound from example 16a) with trifluoroacetic acid using the method given in example 1g). When this was done, 890 mg (1.46 mmol) of the compound from example 16a) gave rise to 510 mg of the desired title compound in the form of a white solid.

M.p.: 66° C.

$R_f$ (SiO$_2$, EA/n-heptane 1:1)=0.20

MS (ESI): m/z=553 [M+H]$^+$ c) Methyl 2-N-(3-methoxycarbonylpropionyl)-2-N-[4-[2-(n-butyloxycarbonylsulfonamido)-5-isobutyl-3-thienyl]benzyl]amino-3-methyl-L-butyrate The title compound was prepared by reacting the compound from example 16b) with n-butyl chloroformate using the method given in example 1h). When this was done, 240 mg (0.43 mmol) of the compound from example 16b) and 547 µl (4.34 mmol) of n-butyl chloroformate gave rise to 260 mg of the desired title compound in the form of a pale yellow amorphous foam.

$R_f$ (SiO$_2$, EA/n-heptane 1:1)=0.11

MS (ESI): m/z=653 [M+H]$^+$

EXAMPLE 17

2-N-(3-Carboxypropionyl)-2-N-[4-[2-(n-butyloxycarbonylsulfonamido)-5-isobutyl-3-thienyl]benzyl]amino-3-methyl-L-butyric acid

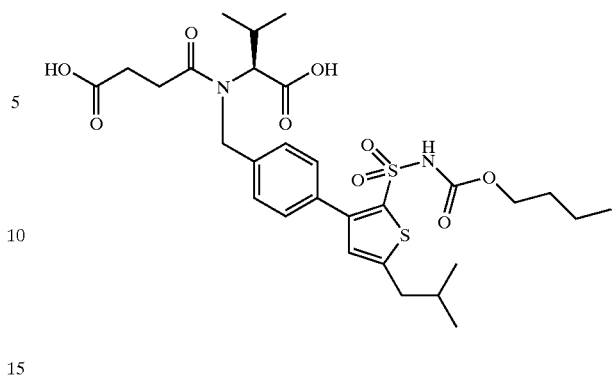

The title compound was prepared by treating the compound from example 16c) with sodium hydroxide solution using the method given in example 6). When this was done, 208 mg (0.32 mmol) of the compound from example 16c) gave rise to 170 mg of the desired title compound in the form of a white solid.

M.p.: 66° C.

$R_f$ (SiO$_2$, EA/n-heptane 4:1)=0.05

MS (ESI): m/z=625 [M+H]$^+$

EXAMPLE 18

Methyl 2-N-(3-methoxycarbonylpropionyl)-2-N-[4-[2-(ethylaminocarbonylsulfonamido)-5-isobutyl-3-thienyl]benzyl]amino-3-methyl-L-butyrate

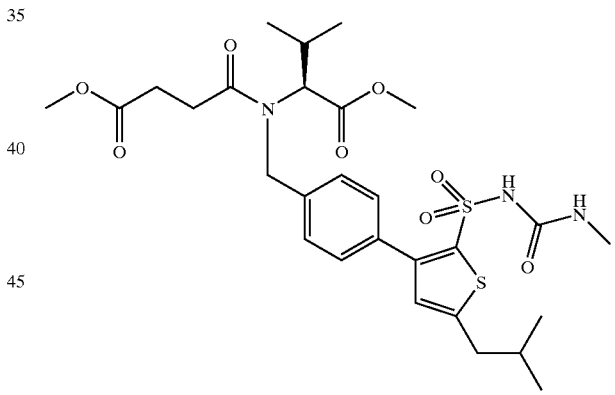

The title compound was prepared from the compound from example 16b) using the method given in example 14). 238 mg (0.43 mmol) of the compound from example 16b) gave rise to 180 mg of the title compound as a white solid.

M.p.: 158° C.

$R_f$ (SiO$_2$, EA/n-heptane 4:2)=0.09

MS (FAB): m/z=610 [M+H]$^+$

EXAMPLE 19

2-N-(3-Carboxypropionyl)-2-N-[4-[2-(ethylaminocarbonylsulfonamido)-5-isobutyl-3-thienyl]benzyl]amino-3-methyl-L-butyric acid

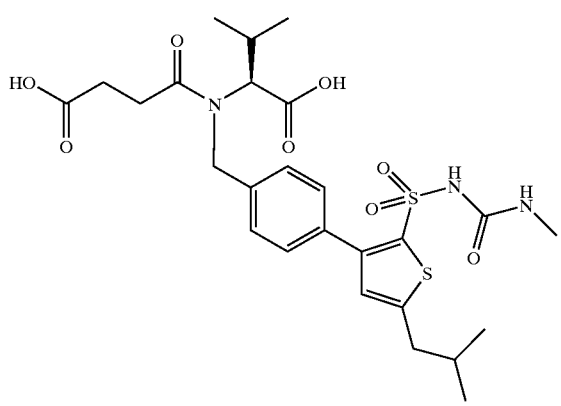

The title compound was prepared by treating the compound from example 18) with sodium hydroxide solution using the method given in example 6). When this was done, 125 mg (0.21 mmol) of the compound from example 18) gave rise to 105 mg of the desired title compound in the form of a white solid.
M.p.: 128° C.
$R_f$ (SiO$_2$, CH$_2$Cl$_2$/MeOH 18:2)=0.23
MS (ESI): m/z=582 [M+H]$^+$

EXAMPLE 20

Methyl 2-N-benzoyl-2-N-[4-[2-(ethylaminocarbonylsulfonamido)-5-isobutyl-3-thienyl]benzyl]amino-2S-phenylacetate

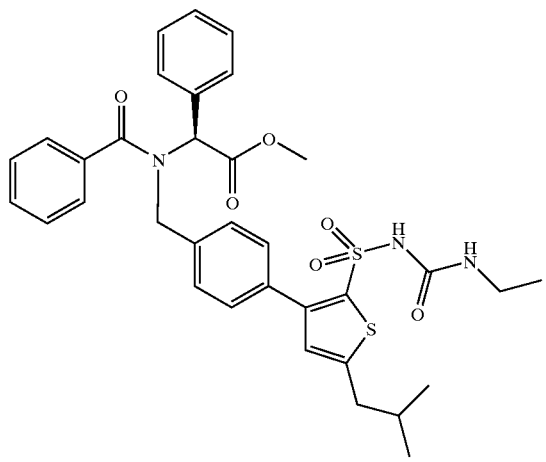

Methyl 2-N-[4-[2-(N-tert-butylsulfonamido)-5-isobutyl-3-thienyl]benzyl]amino-2S-phenylacetate The title compound was prepared by reacting the compound from example 1d) with S-(+)-2-phenylglycine methyl ester hydrochloride using the method given in example 1e). When this was done, 500 mg (1.32 mmol) of the compound from example 1d) and 530.4 mg (2.63 mmol) of S-(+)-2-phenylglycine methyl ester hydrochloride gave rise to 387 mg of the desired title compound in the form of a slightly yellow-colored oil.
$R_f$ (SiO$_2$, EA/n-heptane 1:1)=0.32
MS (ESI): m/z=529 [M+H]$^+$ b) Methyl 2-N-benzoyl-2-N-[4-[2-(N-tert-butylsulfonamido)-5-isobutyl-3-thienyl]benzyl]amino-2S-phenylacetate The title compound was prepared by reacting the compound from example 20a) with benzoyl chloride using the method given in example 1f). When this was done, 193 mg (0.37 mmol) of the compound from example 20a) and 63.8 μl (0.55 mmol) of benzoyl chloride gave rise to 228 mg of the desired title compound in the form of a white amorphous foam.
$R_f$ (SiO$_2$, EA/n-heptane 1:4)=0.12
MS (ESI): m/z=633 [M+H]$^+$ c) Methyl 2-N-benzoyl-2-N-[4-[2-sulfonamido-5-isobutyl-3-thienyl]benzyl]amino-2S-phenylacetate The title, compound was prepared by treating the compound from example 20b) with trifluoroacetic acid using the method given in example 1g). When this was done, 220 mg (0.35 mmol) of the compound from example 20b) gave rise to 132 mg of the desired title compound in the form of a white amorphous foam.
$R_f$ (SiO$_2$, EA/n-heptane 1:1)=0.26
MS (ESI): m/z=577 [M+H]$^+$ d) Methyl 2-N-benzoyl-2-N-[4-[2-(ethylaminocarbonylsulfonamido)-5-isobutyl-3-thienyl]benzyl]amino-2S-phenylacetate The title compound was prepared by reacting the compound from example 20c) with ethyl isocyanate using the method given in example 4). When this was done, 128 mg (0.22 mmol) of the compound from example 20c) gave rise to 88 mg of the title compound in the form of a white amorphous solid.
$R_f$ (SiO$_2$, EA/n-heptane 4:1)=0.35
MS (ESI): m/z=648 [M+H]$^+$

EXAMPLE 21

Methyl 2-N-acetyl-2-N-[4-[2-(ethylaminocarbonylsulfonamido)-5-isobutyl-3-thienyl]benzyl]amino-2S-phenylacetate

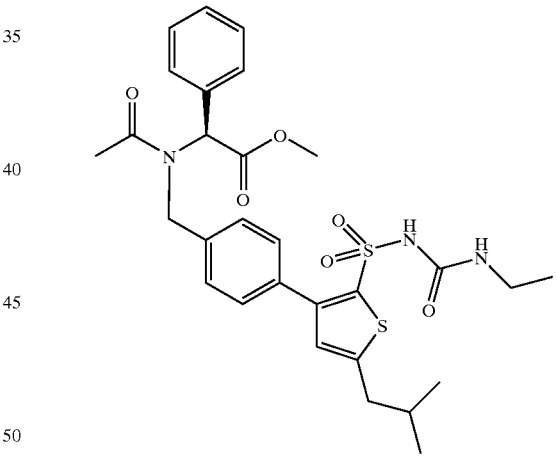

Methyl 2-N-acetyl-2-N-[4-[2-(N-tert-butylsulfonamido)-5-isobutyl-3-thienyl]benzyl]amino-2S-phenylacetate The title compound was prepared by reacting the compound from example 20a) with acetyl chloride using the method given in example 1f). When this was done, 193 mg (0.37 mmol) of the compound from example 20a) and 39.1 μl (0.55 mmol) of acetyl chloride gave rise to 137 mg of the desired title compound in the form of a pale yellow oil.
$R_f$ (SiO$_2$, EA/n-heptane 1:4)=0.17
MS (ESI): m/z=571 [M+H]$^+$ b) Methyl 2-N-acetyl-2-N-[4-[2-sulfonamido-5-isobutyl-3-thienyl]benzyl]amino-2S-phenylacetate The title compound was prepared by treating the compound from example 21a) with trifluoroacetic acid using the method given in example 1g). When this was done, 134 mg (0.24 mmol) of the compound from example 21a) gave rise to 68 mg of the desired title compound in the form of a white amorphous foam.
$R_f$ (SiO$_2$, EA/n-heptane 1:1)=0.10
MS (ESI): m/z=515 [M+H]$^+$ c) Methyl 2-N-acetyl-2-N-[4-[2-(ethylaminocarbonylsulfonamido)-5-isobutyl-3-thienyl]benzyl]amino-2S-phenylacetate The title compound was prepared by reacting the title compound from example 21b) with ethyl isocyanate using the method given in example 4). When this was done, 66 mg (0.13 mmol) of the compound from example 21b) gave rise to 75 mg of the title compound in the form of a white amorphous solid.
$R_f$ (SiO$_2$, EA/n-heptane 4:1)=0.10
MS (ESI): m/z=586 [M+H]$^+$

EXAMPLE 22

Methyl 2-N-benzoyl-2-N-[4-[2-(ethylaminocarbonylsulfonamido)-5-isobutyl-3-thienyl]benzyl]amino-2S-cyclohexylacetate

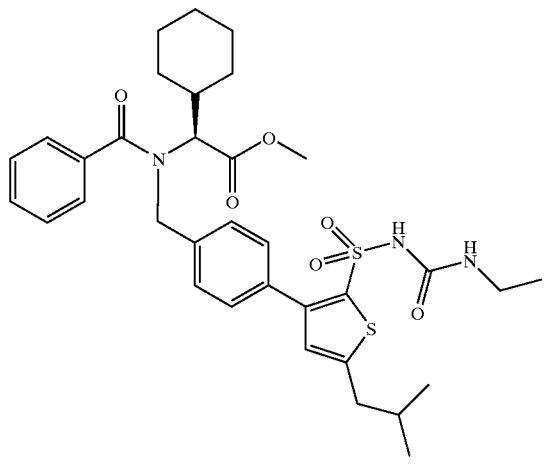

Methyl 2-N-[4-[2-(N-tert-butylsulfonamido)-5-isobutyl-3-thienyl]benzyl]amino-2S-cyclohexylacetate The title compound was prepared by reacting the compound from example 1d) with methyl S-2-amino-2-cyclohexylacetate hydrochloride using the method given in example 1e). When this was done, 500 mg (1.32 mmol) of the compound from example 1d) and 546.2 mg (2.63 mmol) of methyl S-2-amino-2-cyclohexylacetate hydrochloride gave rise to 404 mg of the desired title compound in the form of a slightly yellow-colored oil.
$R_f$ (SiO$_2$, EA/n-heptane 1:4)=0.17
MS (ESI): m/z=535 [M+H]$^+$ b) Methyl 2-N-benzoyl-2-N-[4-[2-(N-tert-butylsulfonamido)-5-isobutyl-3-thienyl]benzyl]amino-2S-cyclohexylacetate The title compound was prepared by reacting the compound from example 22a) with benzoyl chloride using the method given in example 1f). When this was done, 200 mg (0.37 mmol) of the compound from example 22a) and 65.9 µl (0.57 mmol) of benzoyl chloride gave rise to 241 mg of the desired title compound in the form of a white amorphous foam.
$R_f$ (SiO$_2$, EA/n-heptane 1:4)=0.21
MS (ESI): m/z=639 [M+H]$^+$ c) Methyl 2-N-benzoyl-2-N-[4-[2-sulfonamido-5-isobutyl-3-thienyl]benzyl]amino-2S-cyclohexylacetate The title compound was prepared by treating the compound from example 22b) with trifluoroacetic acid using the method given in example 1g). When this was done, 235 mg (0.37 mmol) of the compound from example 22b) gave rise to 130 mg of the desired title compound in the form of a white amorphous foam.
$R_f$ (SiO$_2$, EA/n-heptane 1:1)=0.37
MS (ESI): m/z=583 [M+H]$^+$ d) Methyl 2-N-benzoyl-2-N-[4-[2-(ethylaminocarbonylsulfonamido)-5-isobutyl-3-thienyl]benzyl]amino-2S-cyclohexylacetate The title compound was prepared by reacting the compound from example 22c) with ethyl isocyanate using the method given in example 4). When this was done, 125 mg (0.22 mmol) of the compound from example 22c) gave rise to 90 mg of the title compound in the form of a white amorphous solid.
$R_f$ (SiO$_2$, EA/n-heptane 4:1)=0.37
MS (ESI): m/z=654 [M+H]$^+$

EXAMPLE 23

Methyl 2-N-acetyl-2-N-[4-[2-(ethylaminocarbonylsulfonamido)-5-isobutyl-3-thienyl]benzyl]amino-2S-cyclohexylacetate

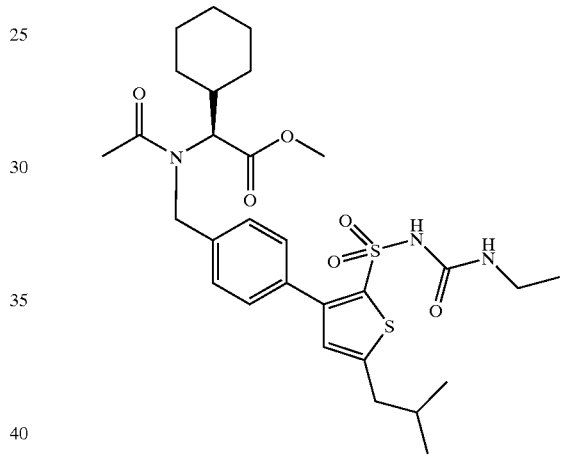

Methyl 2-N-acetyl-2-N-[4-[2-(N-tert-butylsulfonamido)-5-isobutyl-3-thienyl]benzyl]amino-2S-cyclohexylacetate The title compound was prepared by reacting the compound from example 22a) with acetyl chloride using the method given in example 1f). When this was done, 200 mg (0.37 mmol) of the compound from example 22a) and 40.4 µl (0.57 mmol) of acetyl chloride gave rise to 117 mg of the desired title compound in the form of a yellow oil.
$R_f$ (SiO$_2$, EA/n-heptane 1:4)=0.25
MS (ESI): m/z=577 [M+H]$^+$ b) Methyl 2-N-acetyl-2-N-[4-[2-sulfonamido-5-isobutyl-3-thienyl]benzyl]amino-2S-cyclohexylacetate The title compound was prepared by treating the compound from example 23a) with trifluoroacetic acid using the method given in example 1g). When this was done, 114 mg (0.20 mmol) of the compound from example 23a) gave rise to 75 mg of the desired title compound in the form of a pale yellow amorphous foam.
$R_f$ (SiO$_2$, EA/n-heptane 1:1)=0.16
MS (ESI): m/z=521 [M+H]$^+$ c) Methyl 2-N-acetyl-2-N-[4-[2-(ethylaminocarbonylsulfonamido)-5-isobutyl-3-thienyl]benzyl]amino-2S-cyclohexylacetate The title compound was prepared by reacting the compound from example 23b) with ethyl isocyanate using the method given in example 4). When this was done, 72 mg (0.14 mmol) of the compound from example 23b) gave rise to 77 mg of the title compound in the form of a white amorphous solid.
R$_f$ (SiO$_2$, EA/n-heptane 2:1)=0.18
MS (ESI): m/z=592 [M+H]$^+$

EXAMPLE 24

2-Cyclohexyl-N-(2-methoxyethyl)-N-[4-[2-(n-butyloxycarbonylsulfonamido)-5-isobutyl-3-thienyl]benzyl]acetamide

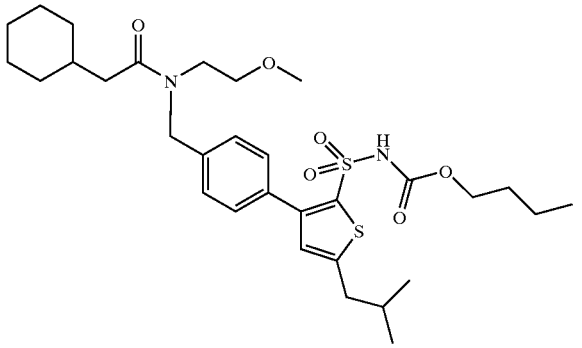

N-[4-[2-(N-tert-Butylsulfonamido)-5-isobutyl-3-thienyl]benzyl]-2-methoxyethylamine The title compound was prepared by reacting the compound from example 1d) with 2-methoxyethylamine using the method given in example 1e). When this was done, 600 mg (1.58 mmol) of the compound from example 1d) and 275 µl (1.58 mmol) of 2-methoxyethylamine gave rise to 342 mg of the desired title compound in the form of a slightly yellow-colored amorphous foam.
R$_f$ (SiO$_2$, EA/n-heptane 1:1)=0.05
MS (ESI): m/z=439 [M+H]$^+$ b) 2-Cyclohexyl-N-(2-methoxyethyl)-N-[4-[2-(N-tert-butylsulfonamido)-5-isobutyl-3-thienyl]benzyl]acetamide A solution of 155 mg (0.36 mmol) of the compound from example 24a), 51 µl (0.36 mmol) of 2-cyclohexylacetic acid, 125 µl (0.72 mmol) of N-ethyldiisopropylamine and 120 mg (0.36 mmol) of O-(cyano)(ethoxycarbonyl)methyleneamino-1,1,3,3-tetramethyluronium tetrafluoroborate (TOTU) in 8 ml of abs. DMF was stirred at RT for 2 h. The solvent was subsequently removed in a vacuum and the residue which remained was taken up in CH$_2$Cl$_2$/water (1:1) and the organic phase was separated off. After drying over Na$_2$SO$_4$, concentrating and chromatographically purifying the remaining residue on SiO$_2$ using EA/n-heptane as the eluent, 185 mg of the desired title compound were obtained in the form of a pale yellow oil.
R$_f$ (SiO$_2$, EA/n-heptane 1:1)=0.27
MS (ESI): m/z=563 [M+H]+ c) 2-Cyclohexyl-N-(2-methoxyethyl)-N-[4-[2-sulfonamido-5-isobutyl-3-thienyl]benzyl]acetamide The title compound was prepared by treating the compound from example 24b) with trifluoroacetic acid using the method given in example 1g). When this was done, 183 mg (0.32 mmol) of the compound from example 24b) gave rise to 108 mg of the desired title compound in the form of a white amorphous foam.
R$_f$ (SiO$_2$, EA/n-heptane 1:1)=0.13
MS (ESI): m/z=507 [M+H]$^+$ d) 2-Cyclohexyl-N-(2-methoxyethyl)-N-[4-[2-(n-butyloxycarbonylsulfonamido)-5-isobutyl-3-thienyl] benzyl]acetamide The title compound was prepared by reacting the compound from example 24c) with n-butyl chloroformate using the method given in example 1h). When this was done, 50. mg (0.10 mmol) of the compound from example 24c) and 124 µl (1.00 mmol) of n-butyl chloroformate gave rise to 46 mg of the desired title compound in the form of a pale yellow amorphous foam.
R$_f$ (SiO$_2$, EA/n-heptane 1:1)=0.14
MS (ESI): m/z=607 [M+H]$^+$

EXAMPLE 25

2-Cyclohexyl-N-(2-methoxyethyl)-N-[4-[2-(ethylaminocarbonylsulfonamido)-5-isobutyl-3-thienyl]benzyl]acetamide

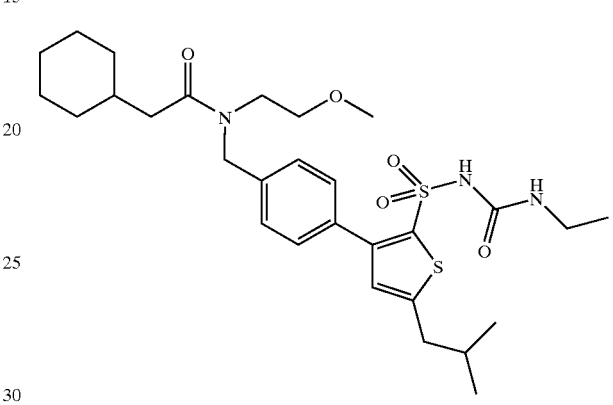

The title compound was prepared by reacting the compound from example 24c) with ethyl isocyanate using the method given in example 4). When this was done, 58 mg (0.11 mmol) of the compound from example 24c) gave rise to 60 mg of the title compound in the form of a white solid.
M.p.: 950° C.
R$_f$ (SiO$_2$, EA/n-heptane 1:1)=0.06
MS (ESI): m/z=578 [M+H]$^+$

EXAMPLE 26

2-Cyclohexyl-N-cyclopropyl-N-[4-[2-(n-butyloxycarbonylsulfonamido)-5-isobutyl-3-thienyl]benzyl]acetamide

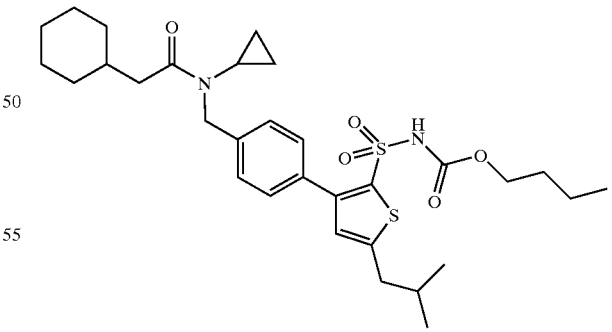

N-[4-[2-(N-tert.-Butylsulfonamido)-5-isobutyl-3-thienyl]benzyl]cyclopropylamine
The title compound was prepared by reacting the title compound from example 1d) with cyclopropylamine using the method given in example 1e). When this was done, 1.20 g (3.16 mmol) of the compound from example 1d) and 442 µl (6.32 mmol) of cyclopropylamine gave rise to 852 mg of the desired title compound in the form of a slightly yellow-colored, amorphous foam.
$R_f$ (SiO$_2$, EA/n-heptane 1:1)=0.10
MS (ESI): m/z=421 [M+H]$^+$ b) 2-Cyclohexyl-N-cyclopropyl-N-[4-[2-(N-tert-butylsulfonamido)-5-isobutyl-3-thienyl]benzyl]acetamide
The title compound was prepared by reacting the compound from example 26a) with 2-cyclohexylacetic acid using the method given in example 24b). When this was done, 150 mg (0.36 mmol) of the compound from example 26a) gave rise to 172 mg of the desired title compound as a white amorphous foam.
$R_f$ (SiO$_2$, EA/n-heptane 1:1)=0.38
MS (ESI): m/z=545 [M+H]$^+$ c) 2-Cyclohexyl-N-cyclopropyl-N-[4-[2-sulfonamido-5-isobutyl-3-thienyl]benzyl]acetamide The title compound was prepared by treating the compound from example 26b) with trifluoroacetic acid using the method given in example 1g). When this was done, 170 mg (0.31 mmol) of the compound from example 26b) gave rise to 120 mg of the desired title compound in the form of a white amorphous foam.
$R_f$ (SiO$_2$, EA/n-heptane 1:1)=0.24
MS (ESI): m/z=489 [M+H]$^+$ d) 2-Cyclohexyl-N-cyclopropyl-N-[4-[2-(n-butyloxycarbonylsulfonamido)-5-isobutyl-3-thienyl]benzyl]acetamide The title compound was prepared by reacting the compound from example 26c) with n-butyl chloroformate using the method given in example 1h). When this was done, 60 mg (0.12 mmol) of the compound from example 26c) and 154 µl (1.23 mmol) of n-butyl chloroformate gave rise to 66 mg of the desired title compound in the form of a pale yellow amorphous foam.
$R_f$ (SiO$_2$, EA/n-heptane 1:1)=0.24
MS (ESI): m/z=589 [M+H]$^+$

EXAMPLE 27

2-Cyclohexyl-N-cyclopropyl-N-[4-[2-(ethylaminocarbonylsulfonamido)-5-isobutyl-3-thienyl]benzyl]acetamide

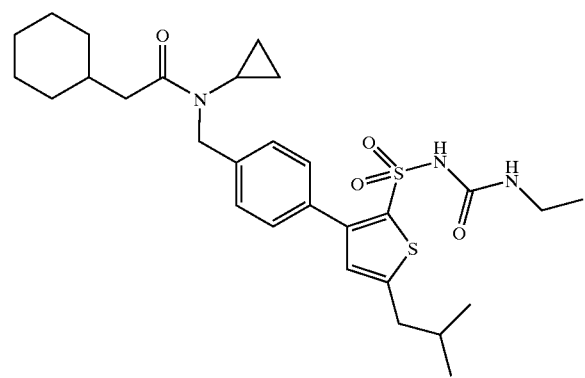

The title compound was prepared by reacting the compound from example 26c) with ethyl isocyanate using the method given in example 4). When this was done, 60 mg (0.12 mmol) of the compound from example 26c) gave rise to 66 mg of the title compound in the form of a white solid. M.p.: 103° C.
$R_f$ (SiO$_2$, EA/n-heptane 1:1)=0.17
MS (ESI): m/z=560 [M+H]$^+$

What is claimed is:
1. A method for the treatment of endothelial dysfunction, which comprises administering to a patient in need thereof a pharmaceutically effective amount of one or more compounds of formula (I):

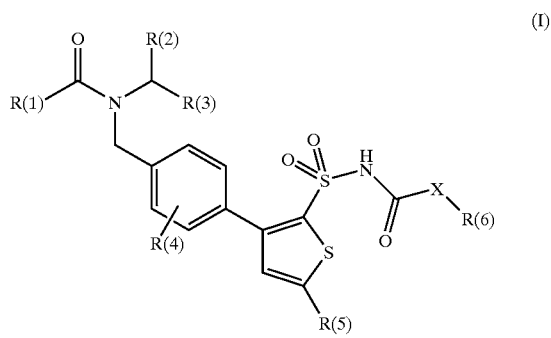

in which the indicated radicals have the following meanings:
R(1) is chosen from among
1. (C$_1$–C$_5$)-alkyl, unsubstituted or substituted by a radical chosen from among NH$_2$, halogen, O—(C$_1$–C$_3$)-alkyl, CO—O—(C$_1$–C$_3$)-alkyl and CO$_2$H;
2. (C$_3$–C$_8$)-cycloalkyl;
3. (C$_1$–C$_3$)-alkyl-(C$_3$–C$_8$)-cycloalkyl;
4. (C$_6$–C$_{10}$)-aryl, unsubstituted or substituted by a radical chosen from halogen and O—(C$_1$–C$_3$)-alkyl;
5. (C$_1$–C$_3$)-alkyl-(C$_6$–C$_{10}$)-aryl, where the aryl radical is unsubstituted or substituted by a radical chosen from halogen and O—(C$_1$–C$_3$)-alkyl;
6. (C$_1$–C$_5$)-heteroaryl; and
7. (C$_1$–C$_3$)-alkyl-(C$_1$–C$_5$)-heteroaryl;

R(2) is chosen from among
1. hydrogen;
2. (C$_1$–C$_6$)-alkyl, unsubstituted or substituted by a radical chosen from halogen and O—(C$_1$–C$_3$)-alkyl;
3. (C$_3$–C$_8$)-cycloalkyl;
4. (C$_1$–C$_3$)-alkyl-(C$_3$–C$_8$)-cycloalkyl;
5. (C$_6$–C$_{10}$)-aryl, unsubstituted or substituted by a radical chosen from among halogen, O—(C$_1$–C$_3$)-alkyl and CO—O—(C$_1$–C$_3$)-alkyl; and
6. (C$_{1-C3}$)-alkyl-(C$_6$–C$_{10}$)-aryl, unsubstituted or substituted by a radical chosen from halogen and O—(C$_1$–C$_3$)-alkyl;

R(3) is chosen from among
1. hydrogen;
2. COOH; and
3. COO—(C$_1$–C$_4$)-alkyl;

R(4) is chosen from among
1. hydrogen;
2. halogen; and
3. (C$_1$–C$_4$-alkyl;

R(5) is chosen from
1. hydrogen, and
2. (C$_1$–C$_6$)-alkyl;

R(6) is chosen from among
1. hydrogen;
2. (C$_1$–C$_6$)-alkyl;
3. (C$_1$–C$_3$)-alkyl-(C$_3$–C$_8$)-cycloalkyl; and
4. (C$_2$–C$_6$)-alkenyl;

X is chosen from
1. oxygen, and
2. NH;

in all the stereoisomeric forms thereof, and mixtures thereof in all ratios, and the physiologically tolerated salts thereof.

\* \* \* \* \*

UNITED STATES PATENT AND TRADEMARK OFFICE
CERTIFICATE OF CORRECTION

PATENT NO.        : 6,984,660 B2  
APPLICATION NO.   : January 10, 2006  
DATED             : 10/310055  
INVENTOR(S)       : Holger Heitsch Page 1 of 1

It is certified that error appears in the above-identified patent and that said Letters Patent is hereby corrected as shown below:

In claim 1, column 36, line 42, "$(C_{1-C3})$-alkyl-$(C_6-C_{10})$-aryl," should read --$(C_1-C_3)$-alkyl-$(C_6-C_{10})$-aryl,--.

In claim 1, column 36, line 53, "$(C_1-C_4$-alkyl;" should read --$(C_1-C_4)$-alkyl;--.

Signed and Sealed this

Twenty-fifth Day of December, 2007

JON W. DUDAS  
*Director of the United States Patent and Trademark Office*

UNITED STATES PATENT AND TRADEMARK OFFICE
CERTIFICATE OF CORRECTION

PATENT NO. : 6,984,660 B2  
APPLICATION NO. : 10/310055  
DATED : January 10, 2006  
INVENTOR(S) : Holger Heitsch It is certified that error appears in the above-identified patent and that said Letters Patent is hereby corrected as shown below:

In claim 1, column 36, line 42, "$(C_{1-C3})$-alkyl-$(C_6-C_{10})$-aryl," should read --$(C_1-C_3)$-alkyl-$(C_6-C_{10})$-aryl,--.

In claim 1, column 36, line 53, "$(C_1-C_4$-alkyl;" should read --$(C_1-C_4)$-alkyl;--.

This certificate supersedes the Certificate of Correction issued December 25, 2007.

Signed and Sealed this

Twenty-ninth Day of January, 2008

JON W. DUDAS  
*Director of the United States Patent and Trademark Office*